US012778571B2

(12) United States Patent
Patel et al.

(10) Patent No.: US 12,778,571 B2
(45) Date of Patent: Nov. 3, 2026

(54) METHOD OF SOFT ANCHOR KNOTLESS REPAIR

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Nehal Navinbhai Patel, Boston, MA (US); Jon-Paul Rogers, North Smithfield, RI (US); Mark E. Housman, North Attleboro, MA (US)

(73) Assignees: Smith & Nephew, Inc., Memphis, TN (US); Smith & Nephew Orthopaedics AG, Zug (CH); Smith & Nephew Asia Pacific Pte. Limited, Singapore (SG)

( * ) Notice: Subject to any disclaimer, the term of this patent is extended or adjusted under 35 U.S.C. 154(b) by 982 days.

(21) Appl. No.: 17/979,588

(22) Filed: Nov. 2, 2022

(65) Prior Publication Data

US 2023/0133232 A1 May 4, 2023

Related U.S. Application Data

(60) Provisional application No. 63/370,729, filed on Aug. 8, 2022, provisional application No. 63/357,181, filed on Jun. 30, 2022, provisional application No. 63/275,493, filed on Nov. 4, 2021, provisional application No. 63/275,491, filed on Nov. 4, 2021.

(51) Int. Cl.
*A61B 17/04* (2006.01)

(52) U.S. Cl.
CPC .. *A61B 17/0401* (2013.01); *A61B 2017/0414* (2013.01); *A61B 2017/0464* (2013.01)

(58) Field of Classification Search
CPC .................... A61B 17/0401; A61B 2017/0414
See application file for complete search history.

(56) References Cited

U.S. PATENT DOCUMENTS 5,366,443 A 11/1994 Eggers et al.
5,374,261 A 12/1994 Yoon
(Continued)

FOREIGN PATENT DOCUMENTS

CN 101073508 A 11/2007
CN 101442944 A 5/2009
(Continued)

OTHER PUBLICATIONS

Arthrex, Fibertak SpeedBridge Rotator Cuff Repair Surgical Technique, 2022, 16 pgs, Arthrex.com.
(Continued)

*Primary Examiner* — Erin McGrath
(74) *Attorney, Agent, or Firm* — Kate Ryland Tetzlaff

(57) ABSTRACT

Methods of tissue repair with a knotless tissue repair construct system is disclosed. System may include multiple anchor constructs that are soft anchor constructs. The multiple anchor constructs may include at least one knotless construct and may be inserted separately and coupled to each other as part of the method. The method may form a knotless all-suture staple construct. The method may form a knotless all-suture construct in a chain configuration. The method may include coupling a graft or bio-inductive material to the repair site. The method may include augmenting a ligament repair.

18 Claims, 26 Drawing Sheets

(56) References Cited

U.S. PATENT DOCUMENTS

| | | | |
|---|---|---|---|
| 5,375,588 | A | 12/1994 | Yoon |
| 5,380,277 | A | 1/1995 | Phillips |
| 5,380,316 | A | 1/1995 | Aita et al. |
| 5,389,096 | A | 2/1995 | Aita et al. |
| 5,395,312 | A | 3/1995 | Desai |
| 5,419,767 | A | 5/1995 | Eggers et al. |
| 5,954,716 | A | 9/1999 | Sharkey et al. |
| 5,990,378 | A | 11/1999 | Ellis |
| 6,203,572 | B1 | 3/2001 | Johnson et al. |
| 6,296,659 | B1 | 10/2001 | Foerster |
| 6,511,498 | B1 | 1/2003 | Fumex |
| 6,585,730 | B1 * | 7/2003 | Foerster ................ A61F 2/0805 411/80 |
| 6,616,684 | B1 | 9/2003 | Vidlund et al. |
| 6,946,003 | B1 | 9/2005 | Wolowacz et al. |
| 6,949,096 | B2 | 9/2005 | Davison et al. |
| 7,070,858 | B2 | 7/2006 | Shalaby et al. |
| 7,217,279 | B2 | 5/2007 | Reese |
| 7,229,441 | B2 | 6/2007 | Trieu et al. |
| 7,285,124 | B2 | 10/2007 | Foerster |
| 7,306,417 | B2 | 12/2007 | Dorstewitz |
| 7,390,332 | B2 | 6/2008 | Selvitelli et al. |
| 7,582,105 | B2 | 9/2009 | Kolster |
| 7,648,524 | B2 | 1/2010 | Zhang et al. |
| 7,740,657 | B2 | 6/2010 | Brown, Jr. et al. |
| 7,749,250 | B2 | 7/2010 | Stone et al. |
| 7,766,939 | B2 | 8/2010 | Yeung et al. |
| 7,857,830 | B2 | 12/2010 | Stone et al. |
| 7,892,256 | B2 | 2/2011 | Grafton et al. |
| 7,905,904 | B2 | 3/2011 | Stone et al. |
| 7,909,851 | B2 | 3/2011 | Stone et al. |
| 7,995,904 | B2 | 8/2011 | Mirsky et al. |
| 8,088,130 | B2 | 1/2012 | Kaiser et al. |
| 8,118,836 | B2 | 2/2012 | Denham et al. |
| 8,172,901 | B2 | 5/2012 | Altman et al. |
| 8,267,959 | B2 | 9/2012 | David |
| 8,292,921 | B2 | 10/2012 | Stone et al. |
| 8,303,604 | B2 | 11/2012 | Stone et al. |
| 8,337,525 | B2 | 12/2012 | Stone et al. |
| 8,361,113 | B2 | 1/2013 | Stone et al. |
| 8,465,522 | B2 | 6/2013 | Burkhart |
| 8,506,597 | B2 | 8/2013 | Kaiser et al. |
| 8,562,647 | B2 | 10/2013 | Kaiser et al. |
| 8,562,847 | B2 | 10/2013 | Yagi et al. |
| 8,608,777 | B2 | 12/2013 | Kaiser et al. |
| 8,790,369 | B2 | 7/2014 | Orphanos et al. |
| 8,828,053 | B2 | 9/2014 | Sengun et al. |
| 8,881,635 | B2 | 11/2014 | Martin |
| 8,961,560 | B2 | 2/2015 | Avelar et al. |
| 9,101,355 | B2 | 8/2015 | Lantz et al. |
| 9,107,653 | B2 | 8/2015 | Sullivan |
| 9,173,645 | B2 | 11/2015 | Overes et al. |
| 9,192,373 | B2 | 11/2015 | Sengun |
| 9,237,888 | B2 | 1/2016 | Sengun et al. |
| 9,247,936 | B2 | 2/2016 | Sengun et al. |
| 9,301,745 | B2 | 4/2016 | Dreyfuss |
| 9,320,512 | B2 | 4/2016 | Dooney, Jr. |
| 9,345,471 | B2 | 5/2016 | Sullivan |
| 9,345,567 | B2 | 5/2016 | Sengun |
| 9,421,008 | B2 | 8/2016 | Burkhart et al. |
| 9,445,803 | B2 | 9/2016 | Marchand et al. |
| 9,492,158 | B2 | 11/2016 | Stone et al. |
| 9,504,462 | B2 | 11/2016 | Dooney, Jr. et al. |
| 9,532,777 | B2 | 1/2017 | Kaiser et al. |
| 9,615,821 | B2 | 4/2017 | Sullivan |
| 9,687,222 | B2 | 6/2017 | Dreyfuss et al. |
| 9,724,090 | B2 | 8/2017 | Kaiser et al. |
| 9,801,620 | B2 | 10/2017 | Kaiser et al. |
| 9,814,454 | B2 | 11/2017 | Sugimoto et al. |
| 9,855,029 | B2 | 1/2018 | Sullivan |
| 9,867,607 | B2 | 1/2018 | Sullivan |
| 9,962,149 | B2 | 5/2018 | Brown |
| 9,962,150 | B2 | 5/2018 | Rodriguez et al. |
| 10,004,489 | B2 | 6/2018 | Kaiser et al. |
| 10,004,495 | B2 | 6/2018 | Dimatteo et al. |
| 10,022,118 | B2 | 7/2018 | Norton et al. |
| 10,058,319 | B2 | 8/2018 | Konrath et al. |
| 10,070,856 | B1 | 9/2018 | Black et al. |
| 10,098,629 | B2 | 10/2018 | Kaiser et al. |
| 10,136,884 | B2 | 11/2018 | Graul et al. |
| 10,154,837 | B2 | 12/2018 | Stone et al. |
| 10,182,806 | B2 | 1/2019 | Foerster |
| 10,251,637 | B2 | 4/2019 | Stone et al. |
| 10,271,833 | B2 | 4/2019 | Sengun |
| 10,292,694 | B2 | 5/2019 | Graul et al. |
| 10,363,025 | B2 | 7/2019 | Lantz et al. |
| 10,368,856 | B2 | 8/2019 | Stone et al. |
| 10,376,259 | B2 | 8/2019 | Bonutti et al. |
| 10,441,269 | B1 | 10/2019 | Bonutti et al. |
| 10,492,776 | B2 | 12/2019 | Dreyfuss et al. |
| RE47,811 | E | 1/2020 | Sullivan et al. |
| 10,524,776 | B2 | 1/2020 | Dreyfuss |
| 10,542,967 | B2 | 1/2020 | Kaiser et al. |
| 10,575,842 | B2 | 3/2020 | Lund |
| 10,595,845 | B2 | 3/2020 | Burkhart et al. |
| 10,595,851 | B2 | 3/2020 | Kaiser et al. |
| 10,631,847 | B2 | 4/2020 | Hart |
| 10,695,046 | B2 | 6/2020 | Sugimoto et al. |
| 10,736,620 | B2 | 8/2020 | Dreyfuss |
| 10,849,734 | B2 | 12/2020 | Holowecky et al. |
| 10,905,409 | B2 | 2/2021 | Brown et al. |
| 10,966,705 | B2 | 4/2021 | Rodriguez et al. |
| 10,973,622 | B2 | 4/2021 | Mackay |
| 11,116,498 | B2 | 9/2021 | Martin |
| 11,141,149 | B2 | 10/2021 | Dimatteo et al. |
| 11,219,446 | B2 | 1/2022 | Bonutti et al. |
| 11,259,794 | B2 | 3/2022 | Stone et al. |
| 11,272,915 | B2 | 3/2022 | Sengun |
| 11,311,287 | B2 | 4/2022 | Stone et al. |
| 11,331,094 | B2 | 5/2022 | Graul et al. |
| 11,427,869 | B2 | 8/2022 | Regev et al. |
| 11,457,958 | B2 | 10/2022 | Bonutti |
| 11,464,505 | B2 | 10/2022 | Burkhart et al. |
| 11,471,147 | B2 | 10/2022 | Kaiser et al. |
| 11,471,266 | B2 | 10/2022 | Mackay |
| 11,497,484 | B2 | 11/2022 | Lund |
| 11,517,300 | B2 | 12/2022 | Lantz et al. |
| 11,529,236 | B2 | 12/2022 | Dekel et al. |
| 11,534,157 | B2 | 12/2022 | Norton |
| 11,589,859 | B2 | 2/2023 | Kaiser et al. |
| 11,612,391 | B2 | 3/2023 | Stone et al. |
| 11,684,477 | B2 | 6/2023 | Dekel et al. |
| 12,075,999 | B2 | 9/2024 | Benedict et al. |
| 12,167,845 | B2 | 12/2024 | Holmes, Jr. |
| 12,239,309 | B2 | 3/2025 | Dong et al. |
| 12,251,100 | B2 | 3/2025 | Norton et al. |
| 2002/0029036 | A1 | 3/2002 | Goble et al. |
| 2002/0120270 | A1 | 8/2002 | Trieu et al. |
| 2004/0012245 | A1 | 1/2004 | Ptasinski |
| 2004/0122456 | A1 | 6/2004 | Saadat et al. |
| 2004/0122473 | A1 | 6/2004 | Ewers et al. |
| 2004/0267362 | A1 | 12/2004 | Hwang et al. |
| 2005/0137624 | A1 | 6/2005 | Fallman |
| 2005/0192581 | A1 | 9/2005 | Molz et al. |
| 2006/0015108 | A1 | 1/2006 | Bonutti |
| 2006/0025800 | A1 | 2/2006 | Suresh |
| 2006/0178683 | A1 | 8/2006 | Shimoji et al. |
| 2006/0271073 | A1 | 11/2006 | Lam et al. |
| 2007/0010857 | A1 | 1/2007 | Sugimoto et al. |
| 2007/0083236 | A1 | 4/2007 | Sikora et al. |
| 2007/0219557 | A1 | 9/2007 | Bourque et al. |
| 2008/0051836 | A1 | 2/2008 | Foerster et al. |
| 2008/0188936 | A1 | 8/2008 | Ball |
| 2008/0300683 | A1 | 12/2008 | Altman et al. |
| 2008/0312689 | A1 | 12/2008 | Denham et al. |
| 2009/0062847 | A1 | 3/2009 | Ken |
| 2009/0082805 | A1 | 3/2009 | Kaiser et al. |
| 2009/0138042 | A1 | 5/2009 | Thal |
| 2009/0240335 | A1 | 9/2009 | Arcenio et al. |
| 2009/0312776 | A1 | 12/2009 | Kaiser et al. |
| 2009/0318961 | A1 | 12/2009 | Stone et al. |
| 2010/0063541 | A1 | 3/2010 | Brunelle et al. |
| 2010/0087857 | A1 | 4/2010 | Stone et al. |
| 2010/0094314 | A1 | 4/2010 | Hernlund et al. |

(56) References Cited

U.S. PATENT DOCUMENTS

| | | | |
|---|---|---|---|
| 2010/0203155 | A1 | 8/2010 | Wei et al. |
| 2011/0022083 | A1 | 1/2011 | Dimatteo et al. |
| 2011/0022084 | A1 | 1/2011 | Sengun et al. |
| 2011/0098727 | A1 | 4/2011 | Kaiser et al. |
| 2011/0118760 | A1 | 5/2011 | Gregoire et al. |
| 2011/0160767 | A1 | 6/2011 | Stone et al. |
| 2011/0160768 | A1 | 6/2011 | Stone et al. |
| 2011/0208239 | A1 | 8/2011 | Stone et al. |
| 2011/0208240 | A1 | 8/2011 | Stone et al. |
| 2011/0270278 | A1 | 11/2011 | Overes et al. |
| 2012/0004669 | A1 | 1/2012 | Overes et al. |
| 2012/0046693 | A1 | 2/2012 | Denham et al. |
| 2012/0059418 | A1 | 3/2012 | Denham et al. |
| 2012/0150223 | A1 | 6/2012 | Manos et al. |
| 2012/0197271 | A1 | 8/2012 | Astorino et al. |
| 2012/0239085 | A1 | 9/2012 | Schlotterback et al. |
| 2012/0245585 | A1 | 9/2012 | Kaiser et al. |
| 2012/0290002 | A1 | 11/2012 | Astorino |
| 2012/0290004 | A1 | 11/2012 | Lombardo et al. |
| 2013/0029693 | A1 | 1/2013 | Bradley, Jr. |
| 2013/0096612 | A1 | 4/2013 | Zajac |
| 2013/0103082 | A1 | 4/2013 | Kaiser et al. |
| 2013/0110165 | A1 | 5/2013 | Burkhart et al. |
| 2013/0116730 | A1 | 5/2013 | Denham et al. |
| 2013/0123810 | A1 | 5/2013 | Brown et al. |
| 2013/0131722 | A1 | 5/2013 | Marchand et al. |
| 2013/0153810 | A1 | 6/2013 | Sealey et al. |
| 2013/0163810 | A1 | 6/2013 | Wang |
| 2013/0190818 | A1 | 7/2013 | Norton |
| 2013/0237997 | A1 | 9/2013 | Arai et al. |
| 2013/0296895 | A1 | 11/2013 | Sengun |
| 2013/0296896 | A1 | 11/2013 | Sengun |
| 2013/0296934 | A1 | 11/2013 | Sengun |
| 2014/0052178 | A1 | 2/2014 | Dooney, Jr. |
| 2014/0052179 | A1 | 2/2014 | Dreyfuss et al. |
| 2014/0114330 | A1 | 4/2014 | Karasic et al. |
| 2014/0121700 | A1 | 5/2014 | Dreyfuss |
| 2014/0257384 | A1 | 9/2014 | Dreyfuss |
| 2014/0277121 | A1 | 9/2014 | Pilgeram et al. |
| 2014/0277133 | A1 | 9/2014 | Foerster |
| 2014/0316460 | A1 | 10/2014 | Graul et al. |
| 2015/0066081 | A1 | 3/2015 | Martin |
| 2015/0164497 | A1 | 6/2015 | Callison et al. |
| 2015/0173739 | A1* | 6/2015 | Rodriguez ....... A61B 17/06166 606/232 |
| 2015/0201929 | A1 | 7/2015 | Dooney, Jr. et al. |
| 2015/0351739 | A1 | 12/2015 | Napolitano |
| 2016/0000421 | A1 | 1/2016 | Larsen |
| 2016/0270777 | A1 | 9/2016 | Miller et al. |
| 2016/0354078 | A1 | 12/2016 | Overes et al. |
| 2016/0361155 | A1* | 12/2016 | Van Kampen ............ A61F 2/08 |
| 2017/0035554 | A1 | 2/2017 | Mackay |
| 2018/0125472 | A1 | 5/2018 | Dreyfuss |
| 2018/0193015 | A1 | 7/2018 | Denham et al. |
| 2018/0214143 | A1 | 8/2018 | Brown et al. |
| 2018/0221010 | A1* | 8/2018 | Lund .................. A61B 17/0401 |
| 2018/0228484 | A1 | 8/2018 | Rodriguez et al. |
| 2018/0243078 | A1* | 8/2018 | Jastifer ................. A61F 2/0811 |
| 2018/0271523 | A1 | 9/2018 | Dimatteo et al. |
| 2018/0344892 | A1* | 12/2018 | Cotton ............... A61B 17/0401 |
| 2019/0015092 | A1 | 1/2019 | Bosworth |
| 2019/0021719 | A1* | 1/2019 | Dooney ............. A61B 17/0401 |
| 2019/0053834 | A1 | 2/2019 | Bonutti |
| 2019/0117212 | A1 | 4/2019 | Foerster |
| 2019/0223857 | A1 | 7/2019 | Sengun |
| 2019/0231342 | A1 | 8/2019 | Graul et al. |
| 2019/0231348 | A1 | 8/2019 | Stone et al. |
| 2019/0247039 | A1 | 8/2019 | Gregoire |
| 2019/0298345 | A1 | 10/2019 | Denham et al. |
| 2019/0365366 | A1 | 12/2019 | Petry |
| 2020/0015810 | A1 | 1/2020 | Piccirillo |
| 2020/0022693 | A1 | 1/2020 | Lantz et al. |
| 2020/0022701 | A1 | 1/2020 | Crook |
| 2020/0054439 | A1 | 2/2020 | Holowecky et al. |
| 2020/0138429 | A1 | 5/2020 | Dreyfuss et al. |
| 2020/0155139 | A1 | 5/2020 | Bonutti et al. |
| 2020/0187932 | A1 | 6/2020 | Kaiser et al. |
| 2020/0187933 | A1 | 6/2020 | Kaiser et al. |
| 2020/0205799 | A1 | 7/2020 | Burkhart et al. |
| 2020/0268502 | A1 | 8/2020 | Brunsvold et al. |
| 2020/0330088 | A1 | 10/2020 | Sugimoto et al. |
| 2021/0034590 | A1 | 2/2021 | Delight, IV et al. |
| 2021/0100544 | A1 | 4/2021 | Burkhart et al. |
| 2021/0137672 | A1 | 5/2021 | Mackay |
| 2021/0186485 | A1 | 6/2021 | Rodriguez et al. |
| 2021/0228200 | A1 | 7/2021 | Brown et al. |
| 2021/0244401 | A1 | 8/2021 | Burkhart et al. |
| 2021/0275160 | A1 | 9/2021 | Snell et al. |
| 2021/0346148 | A1 | 11/2021 | Hosseini et al. |
| 2022/0008069 | A1 | 1/2022 | Martin |
| 2022/0015757 | A1 | 1/2022 | Stone et al. |
| 2022/0175514 | A1 | 6/2022 | Verma et al. |
| 2022/0218341 | A1 | 7/2022 | Martin |
| 2022/0378409 | A1 | 12/2022 | Zenz-olson et al. |
| 2023/0200799 | A1 | 6/2023 | Rogers et al. |
| 2024/0000445 | A1 | 1/2024 | Gabriel et al. |
| 2024/0081807 | A1 | 3/2024 | Stone et al. |
| 2024/0108381 | A1 | 4/2024 | Southern |
| 2024/0197313 | A1 | 6/2024 | Ninh |
| 2024/0415505 | A1 | 12/2024 | Housman et al. |
| 2025/0072883 | A1 | 3/2025 | Dooney, Jr. et al. |

FOREIGN PATENT DOCUMENTS

| | | | |
|---|---|---|---|
| CN | 101961264 | A | 2/2011 |
| CN | 103327910 | A | 9/2013 |
| CN | 103705280 | A | 4/2014 |
| CN | 108652689 | A | 10/2018 |
| CN | 111182837 | A | 5/2020 |
| CN | 113853170 | A | 12/2021 |
| CN | 216021207 | U | 3/2022 |
| CN | 117017387 | A | 11/2023 |
| CN | 117100340 | A | 11/2023 |
| EP | 2430984 | A1 | 3/2012 |
| EP | 2572648 | A1 | 3/2013 |
| EP | 2662031 | A1 | 11/2013 |
| EP | 2698117 | A1 | 2/2014 |
| EP | 2698128 | A1 | 2/2014 |
| EP | 2774545 | A2 | 9/2014 |
| EP | 2774546 | A1 | 9/2014 |
| EP | 2779913 | A1 | 9/2014 |
| EP | 2995261 | A1 | 3/2016 |
| EP | 3738520 | A2 | 11/2020 |
| EP | 4056125 | A1 | 9/2022 |
| EP | 4464259 | A2 | 11/2024 |
| EP | 4477158 | A1 | 12/2024 |
| FR | 3142337 | A1 | 5/2024 |
| JP | 2012520141 | A | 9/2012 |
| WO | 2012151592 | A2 | 11/2012 |
| WO | 2012151692 | A1 | 11/2012 |
| WO | 2015095524 | A2 | 6/2015 |
| WO | 2016205351 | A1 | 12/2016 |
| WO | 2017160589 | A1 | 9/2017 |
| WO | 2018085663 | A1 | 5/2018 |
| WO | 2020252372 | | 12/2020 |
| WO | 2020252372 | A1 | 12/2020 |
| WO | 2020255372 | A1 | 12/2020 |
| WO | 2021243062 | A1 | 12/2021 |
| WO | 2022185310 | A1 | 9/2022 |
| WO | 2023081171 | A1 | 5/2023 |
| WO | 2024242743 | A1 | 11/2024 |

OTHER PUBLICATIONS

Engebretsen, Lars, et al., "Knee Joint Motion and Ligament Force in Nonaugmented and Augmented Primary Repairs of Anterior Cruciate Ligament Ruptures," The American Journal of Sports Medicine 17, (1989): 706-707, 2 pages, Minneapolis, Minnesota.

Engebretsen, Lars, "Knee Mechancis After Repair of the Anterior Cruciate Ligament—A Cadaver Study of Ligament Augmentation," Acta Orthopaedica Scandinavica, Jan. 1990, 8 pages.

T. Grontvedt, L. Engebretsen, "Comparison Between Two Techniques or Surgical Repair of the Acutely Torn Anterior Cruciate

(56) References Cited

OTHER PUBLICATIONS

Ligament," Scandinavian Journal of Medicine & Science in Sports, 1995; 5: 358-363, 6 pages, Denmark.
Arthrex, Knotless 1.8 FiberTak Soft Anchor for Glenoid Labrum Repair, 2021, Arthrex.com.
Arthrex, Knotless Suture Tak Anchor for Instability Repair, 2021, Arthrex.com.
Arthrex, Rotator Cuff Repair With FiberTak® Soft Anchors, 2025, 8 pages.
International Preliminary Report on Patentability (IPRP) PCT/US2022/048644 dated May 2, 2024 (WO/2023/081171), 13 pages.
International Preliminary Report on Patentability (IPRP) PCT/US2012/065103 dated Feb. 5, 2013 (WO2013074691), 11 pages.
PASTA Lesion: https://www.vumedi.com/video/pasta-repair-knotless-all-suture-anchor-technique/.
Remplissage: https://www.vumedi.com/video/knotless-all-suture-remplissage-with-arthroscopic-bankart-repair/.
Search Report and Written Opinion PCT/US2012/065103 dated Feb. 5, 2013 (WO2013074691), 16 pages.
Search Report and Written Opinion PCT/US2014/071164 dated Jul. 15, 2015 (WO2015095524), 20 pages.
Search Report and Written Opinion PCT/US2022/048644 dated Apr. 13, 2023 (WO2023081171), 18 pages.
Shoulder Restoration System: Arthroscopic Bankart Repair using the Y-Knot™ 1.3mm All-Suture Anchor. Datasheet [online]. ConMed Linvatec, 2011 [retrieved on Nov. 14, 2012]. Retrieved from the Internet: URL: http://dashboard.linvatec.com/filemanager/public/Sports Medicine/Shoulder/Literature/CST 3040 Rev1 Y-Knot Surgical Technique.pdf.
Y-Knot® 1.3mm All-Suture Anchor. Datasheet [online]. ConMed Linvatec, No Date Given. [retrieved on Nov. 14, 2012]. Retrieved from the Internet: URL: http://srs.linvatec.com/SRS_instability_Yknot.php.
International Preliminary Report on Patentability (IPRP) from PCT/US2017/059943 (WO2018/085663) dated May 7, 2019, 12 pages.
International Preliminary Report on Patentability (IPRP) PCT/US2014/071164 (WO2015/095524) dated Jun. 21, 2016, 14 pages.
International Preliminary Report on Patentability (IPRP) PCT/US2020/037574 (WO2020/252372) dated Dec. 14, 2021, 11 pages.
Search Report and Written Opinion from PCT/US2017/059943 (WO2018/085663) dated Jan. 29, 2018, 18 pages.
Search Report and Written Opinion from PCT/US2020/037574 (WO2020/252372) dated Dec. 1, 2020, 20 pages.

* cited by examiner

METHOD OF SOFT ANCHOR KNOTLESS REPAIR

CROSS-REFERENCE TO RELATED APPLICATIONS

This application claims the benefit of U.S. provisional application Ser. No. 63/275,493 filed Nov. 4, 2021, and also U.S. provisional application Ser. No. 63/370,729 filed Aug. 8, 2022, both titled, "All Suture Knotless Repair System". This application is related to commonly owned U.S. provisional application Ser. No. 63/275,491 filed Nov. 4, 2021, and titled, "Knotless Soft Anchor System"; and U.S. provisional application Ser. No. 63/357,181 filed Jun. 30, 2022, and titled, "Knotless Soft Anchor System" and PCT application PT-5834-US-PCT. These applications are all incorporated by reference herein, in their entirety as if reproduced in full below.

FIELD

The present disclosure relates to systems and methods associated with a repair system that may include a knotless soft anchor system.

BACKGROUND

Many orthopedic surgeries involve the use of anchoring devices in procedures for attaching tissues, such as soft tissue to bone. Such procedures include, for example, attaching tendons to bone, bone to bone, tendons to tendons, ligaments or grafts to bone. Anchoring device may also be part of a construct that augments a primary repair. Generally, these procedures rely on the use of polymeric, metal, or biodegradable rigid anchors with suture attached. The suture is passed through the tissue and a knot secures the anchor and tissue together. However, the use of these anchors often requires rigid, hard materials to be placed in tissue such as bone. If the anchors loosen, a surgeon or surgical technician is faced with the problem of having a potentially hard device migrate into a patient's joint, placing the patient at risk for arthritis. Accordingly, an anchor that uses only soft materials may pose less risk of anatomical damage in a joint or body cavity, should they be dislodged post-operatively.

Existing soft flexible anchors available today may be formed with all or substantially all suture or soft flexible material and may include a braided body. Soft anchors may anchor with tissue by deforming or relaxing to a radially or laterally expanded state which may be locked in this expanded state by tying knots. Knot-tying may however add complexity to the procedure, may require a higher level of expertise, may be time consuming, and/or be more anatomically disruptive to surrounding structures. Adding knots may also tend to form what is called a knot stack, which may add bulk and palpability to the repair site. Therefore, there is a need for a soft anchor system that includes a knotless locking construct, avoiding the step of tying a knot and addressing the issues listed herein.

In addition, not all soft anchors are created equal. They may differ in a variety of ways including their deployment consistency, the volume of bone removal required and their fixation strength, depending on the soft anchor construct and mechanisms for deployment. Therefore, there is a need for an improved knotless anchor system that includes a high fixation strength soft anchor, that may be consistently deployed, remove minimal amounts of bone tissue and reliably knotlessly lock. Knotlessly locking may fix the soft anchor in the deployed configuration and/or may knotlessly couple a repair tissue to the soft anchor. The "Q-FIX ◊ All-Suture Anchor", offered for sale by Smith and nephew defines a soft anchor, formed of a tubular braided body that addresses this need. As disclosed in U.S. Pat. No. 9,962,149, titled "Tissue Repair Assembly"; commonly owned and herein incorporated by reference in its entirety, this anchor in cooperation with the insertion system may be deployed to a deployed, bunched up state that provides a high fixation strength.

In addition, a tissue repair may preferably include the use of multiple soft anchors that are coupled together for the repair. The soft anchors may be provided separately and coupled to each other to create a suture staple or suture bridge over or through a target tissue during the procedure. Tissue repair may include creating a suture staple or bridge between at least two bones. Tissue repair may include creating a suture staple or bridge over and/or through a graft, scaffold or bio-inductive material. Tissue repair may repair a joint or two fractured portions of a bone. Some existing systems with multiple anchors may provide the soft anchors preassembled to each other, which may be cumbersome to manage. Some existing systems may deploy the anchors simultaneously or with a single deployment member, with may add complexity and frustrate fixation strength. Some existing systems may require tying of knots after the two or more anchors have been inserted, adding complexity and time to the procedure. Therefore, there is a need for a system and method of repair that includes multiple soft anchors that provides strong fixation strength, avoids the requirement to tie knots and addresses the needs listed.

Definitions

Described herein are tissue repair systems, which use a soft anchor. The tissue repair systems of this disclosure provide a high fixation strength, fixing the soft anchor within bone. The tissue repair system preferably knotlessly locks in a repaired configuration, avoiding the need for the surgeon to tie a knot. The tissue repair system may include at least one suture. The term "suture" may include traditional sutures, that may be either hollow or may include braids along their core, unless were specified. The term "suture" may include equivalent flexible members, such as but not limited to suture tape, flattened suture, cable, ribbon or wire, where appropriate.

"Soft Anchor" is intended to mean a flexible and/or deformable anchor, formed of soft, flexible material, that changes to a more laterally expanded configuration upon deployment. A tensioning member that is operatively coupled through a portion of the soft anchor may be tensioned to laterally expand the soft anchor. The term "soft anchor" does not preclude it from including some select portions that are rigid; only that the soft anchor body is substantially formed from a flexible soft material such as suture or suture tape. In some embodiments, the soft anchor is formed entirely of braided suture. Soft anchors deform to a deployed configuration that changes the soft anchor to a laterally or radially expanded configuration and may also include a longitudinal contraction.

"Deploy" is intended to mean to change the shape of the body of the soft anchor (the "anchor body") such that the anchor body is set, fixed or anchored with/within a tissue. Deploying may increase a lateral dimension of the anchor body to secure it with a tissue. For example, this may fix the soft anchor within a bone hole. To deploy an anchor body changes the anchor to a deployed configuration.

"Lock" or "locked configuration" with respect to a suture construct is intended to mean locking a suture such that the suture may no longer slide in at least one direction. Sliding in this at least one direction for example may loosen a repair tissue that is secured in place. The suture may form a loop including a tissue coupled thereto and the loop perimeter is prevented from sliding and increasing in perimeter size. With respect to an anchor body, a locked configuration is intended to mean locking the anchor body in a deployed configuration to inhibit the anchor body from relaxing/moving out of the deployed configuration.

"Knotlessly locking" or a word stemming derivative therefrom such as knotless locking for example is intended to mean a lock in a surgical construct or anchor system formed without having the tie a knot. A system provided with a pre-formed knot may be defined as knotlessly locking. A system configured to route the suture during operation of the surgical construct to form a knot, is also defined as knotlessly locking. Knotlessly locking may also be achieved by passing at least one suture along a tortuous route through small openings, or through a suture locking passage construct, may also be called Chinese finger traps, finger cinches or locking splices for example. To knotlessly lock the system, some of the sutures may extend through the suture locking passage of either the same suture or another suture, to form a self-locking adjustable suture construct as described herein. Suture locking passage may be selectively elongated, by applying tension to the locking passage to cinch around the suture disposed therein, thereby locking a portion of the adjustable suture construct.

"Transfer member" is a construct or suture that transfers a flexible member, such as a suture through the knotless anchor construct. Transfer member may be a suture or wire.

"Deploying suture" is intended to mean the suture(s) (or equivalent as defined herein) that deploys the soft anchor body, upon tension being applied to the deploying suture. In some embodiments, the deploying suture may also provide other functions.

"Repair Suture" is a suture (or equivalent as defined herein) that repairs the tissue or attaches a tissue or implant.

"Static loop" shall mean a loop that has a perimeter that is not adjustable under normal operating load conditions.

"Working opening" shall mean an opening through a surgical device that is limited in size, so that it presents a challenging force to draw a suture construct including a discontinuity, such as a knot or a splice end of a suture loop therethrough. The "working opening" receives or houses the suture construct therein during normal operation of the surgical device and suture construct. The "working opening" may be an aperture, tunnel, cannulation, passage or shaft bore of a surgical device or devices. The "working opening" has an opening size that may be a diameter, or an equivalent width should the opening be a shape other than a circle. This "working opening" may be minimized in opening size, to generally contribute towards an overall smaller profile surgical device for surgical repair. The surgical device may include openings of varying opening sizes, and some of the openings may not present a challenging force and therefore some of the openings but not all may be "working openings" as defined herein.

A "surgical device" means at least one of a surgical tool or instrument, such as an insertion instrument; an implant such as a tissue anchor that may be rigid or soft; and/or a flexible member such as suture, suture tape, cable, wire, flexible spring, ring or tube.

"Working length" shall mean an entire axial length of the suture loop splice extending from the entrance of the suture through itself at a loop end, through to the splice end.

SUMMARY

Described herein are various improvements in methods and devices for tissue repair with a knotlessly locking construct, that may include a plurality of soft anchor constructs. These and other features and advantages will be apparent from a reading of the following detailed description and a review of the associated drawings. It is to be understood that both the foregoing general description and the following detailed description are explanatory only and are not restrictive of aspects as claimed.

An example method of tissue repair is disclosed, the method including deploying a first soft anchor construct in a first bone portion. The first soft anchor construct includes a first soft anchor with a repair suture and a deploying suture extending therethrough. The deploying suture may be threaded through both the soft anchor and a cannulation of the repair suture defining a knotless suture-locking-passage region of the construct. The knotless suture-locking-passage region is interwoven repeatedly through and along the first soft anchor. Deploying may include tensioning both the repair suture and deploying suture simultaneously. The method also includes deploying a second soft anchor in a second bone portion spaced away from the first bone portion, by tensioning a suture interwoven through the second soft anchor. The repair suture may be passed through or around a repair tissue and/or through or around an implant. The repair suture may be coupled to the second suture and the second suture may be withdrawn through the second soft anchor to remove the second suture from the second soft anchor and replace it with the repair suture. An end of the repair suture may now extend from the second soft anchor proximal end, forming a first link between the two soft anchors. This repair suture end may now be coupled to the deploying suture and the deploying suture withdrawn to remove it from the first soft anchor and replace it with the repair suture. Withdrawing the deploying suture at this stage may draw the repair suture through the knotless suture-locking-passage region interwoven repeatedly through and along the first soft anchor. Now with the repair suture extending within the cannulation of the knotless suture-locking-passage region, tensioning the repair suture may cinch the knotless suture-locking-passage region and knotlessly lock the repair suture.

Some example methods may include obtaining a bio-inductive sheet-like implant and passing the repair suture may include passing it through the bio-inductive sheet-like implant and tensioning the repair suture to knotless lock the repair suture may knotlessly couple the bio-inductive sheet-like implant to the first and second bone portions. The first and second bone portions may be portions of the humerus for repair of the supraspinatus tendon. The first and second bone portions may be portions of a calcaneus bone, for repair of an Achilles tendon. The first and second bone portions may be part of a femur, for repair of a Gluteus Medius. The first bone portion may be a distal end of a fibula and the second bone portion may be the talus and passing the repair suture may pass the repair suture along the Anterior Talofibular Ligament to augment a primary repair of the Anterior Talofibular Ligament.

In some example methods, the first soft anchor may be a tubular body defining a lumen and the knotless suture-locking-passage region is interwoven through a sidewall including at least three passes on a single side of the tubular body lumen, the opposing sidewall of the tubular body absent the repair suture. The first and second soft anchors may both be deployed before passing the repair suture and drawing the repair suture through the second soft anchor. The first and second soft anchors may both be deployed before withdrawing the deploying suture to remove it from the first soft anchor and replace it with the repair suture.

An example method is disclosed for forming a knotless suture staple, the example method including deploying a first soft anchor in a first bone portion. The first soft anchor includes a first repair suture extending therethrough, the first repair suture including a cannulation. The first soft anchor also includes a first deploying suture threaded therethrough and also through the repair suture cannulation defining a first knotless suture-locking-passage region, the first knotless suture-locking-passage region interwoven repeatedly through and along the first soft anchor. Deploying includes applying tension to both the first repair suture and first deploying suture simultaneously. A second soft anchor is also deployed, in a second bone portion, spaced away from the first bone portion. The second soft anchor includes a second repair suture extending therethrough, the second repair suture including a cannulation. The second soft anchor also includes a second deploying suture threaded therethrough and also through the cannulation defining a second knotless suture-locking-passage region, the second knotless suture-locking-passage region interwoven repeatedly through and along the second soft anchor. Deploying includes applying tension to both the second repair suture and second deploying suture.

The method continues with passing the first repair suture through the second soft anchor by coupling the first repair suture to the second deploying suture and withdrawing the second deploying suture to remove the second deploying suture and replace it with the first repair suture. Withdrawing includes drawing the first repair suture through the second knotless suture-locking-passage region. The second repair suture is also passed through the first soft anchor by coupling the second repair suture extending from the second soft anchor to the first deploying suture and withdrawing the first deploying suture to remove it from the first soft anchor and replace it with the second repair suture. Withdrawing also draws the second repair suture through the first knotless suture-locking-passage region. The first and second repair suture may now be tensioned to knotless lock the knotless suture staple.

In some example methods, a bio-inductive sheet-like implant is obtained and tensioning the first and second repair suture to knotless lock the knotless suture staple, staples the bio-inductive sheet-like implant to the first and second bone portions. The first and second bone portions may be portions of the humerus for repair of the supraspinatus tendon. The first and second bone portions may be portions of a calcaneus bone, for repair of an Achilles tendon. The first and second bone portions may be part of a femur, for repair of a Gluteus Medius. The first bone portion may be a distal end of a fibula and the second bone portion may be the talus and passing the repair suture may pass the repair suture along the Anterior Talofibular Ligament to augment a primary repair of the Anterior Talofibular Ligament.

In some example methods, the first repair suture may include a tape portion and passing the first repair suture through or around tissue to be stapled places the tape portion in engagement with the tissue to be repaired. The first and second soft anchors may both define tubular bodies, each tubular body defining a lumen and where the first and second knotless suture-locking-passage regions are interwoven through a single side of the respective tubular body lumens and absent an opposing side of the tubular body lumens. The first and second soft anchors may both be deployed before drawing the first repair suture through the second knotless suture-locking-passage region and also before drawing the second repair suture through the first suture-locking-passage region.

An example method of knotlessly repairing a tissue with a multi-anchor knotless construct is also disclosed, the method including obtaining a first anchor construct and a second anchor construct of the multi-anchor knotless construct. The first anchor construct includes a first soft anchor that is tubular having a proximal end, a distal end, and a lumen coaxial with a soft anchor longitudinal axis. The first anchor construct includes a first repair suture having a first end fixedly coupled to the first soft anchor and a second end extending proximally from the first anchor proximal end, a length of the first repair suture between the first and second end defining a cannulated length, the cannulated length interwoven through a first sidewall of the first soft anchor. The first anchor construct includes a first deploying suture interwoven repeatedly through the first soft anchor and also within the cannulated length of the repair suture that is interwoven through and along the first sidewall. The first anchor construct is inserted into a first bone with a first insertion instrument operatively coupled to the first anchor construct and tension is applied to at least one of the first repair suture and/or first deploying suture to change the first soft anchor to a deployed configuration within the first bone. The second anchor construct of the multi-anchor knotless construct is separate from the first anchor construct and includes a second soft anchor having a proximal end, a distal end, and a longitudinal axis extending therebetween. It also includes a second deploying suture interwoven repeatedly through and along the second anchor, a first and second end of the second deploying suture extending from the second soft anchor proximal end, the second soft anchor being tubular, with a lumen coaxial with the second longitudinal axis. The second anchor construct is inserted into a second bone with a second insertion instrument operatively coupled to the second anchor construct and tension is applied to the second deploying suture to change the second soft anchor to a deployed configuration within the second bone. The first end of the second deploying suture is coupled to the first repair suture second end and tension applied to the second deploying suture second end draws the first repair suture across to the second soft anchor and also through the second soft anchor, replacing the second deploying suture with the first repair suture, defining a first link between the two constructs. The first repair suture extending from the second soft anchor may then be coupled to a snaring end of the first deploying member and tension applied to an opposing end of the first deploying suture to draw the first repair suture back cross to the first soft anchor, through the first soft anchor and through the first repair suture cannulated length interwoven through and along the first soft anchor replacing the first deploying suture with the first repair suture and defining a second link between the two construct. Applying tension to the first repair suture end may knotlessly lock the first and second links.

In some example methods, a third anchor construct may be obtained, the third anchor construct including a third soft anchor having a proximal end, a distal end, and a longitudinal axis extending therebetween and a third deploying suture interwoven repeatedly through and along a first and second sidewall of the third ancho. A first and second end of the third deploying suture may extend from the third soft anchor proximal end. The third soft anchor may be tubular, with a lumen coaxial with the third longitudinal axis and wherein the first and second sidewalls of the third soft anchor are on diametrically opposing sides of the third soft anchor lumen. The third anchor construct may be inserted into a third bone and tension applied on the third deploying suture to change the third soft anchor to a deployed configuration within the third bone. The first end of the second deploying suture may be coupled to the third repair suture second end and tension applied to the second deploying suture second end may draw the third repair suture across to the third soft anchor and also through the second soft anchor, replacing the second deploying suture with the third repair suture, defining a third link. Thereafter, the third repair suture extending from the second soft anchor may be coupled to a snaring end of the third deploying member and tension applied to an opposing end of the third deploying suture to draw the third repair suture back cross to the third soft anchor and also through the third soft anchor and third repair suture cannulated length interwoven through and along the third soft anchor replacing the third deploying suture with the third repair suture and defining a fourth link.

BRIEF DESCRIPTION OF THE DRAWINGS

The disclosure will be more fully understood by reference to the detailed description, in conjunction with the following figures, wherein.

DETAILED DESCRIPTION

Figure 1A:
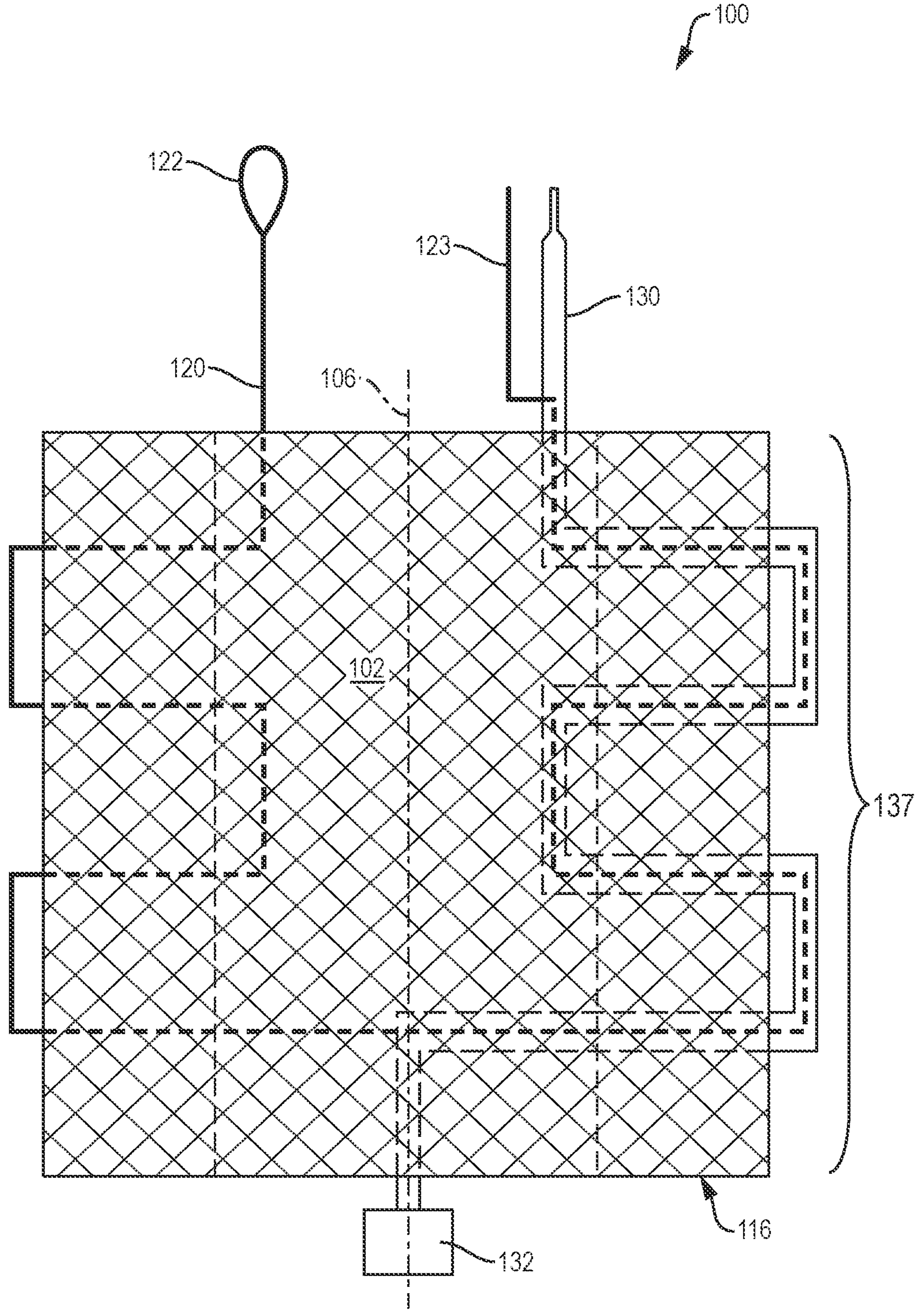
FIG. 1A illustrates a soft anchor knotless construct, in accordance with this disclosure.

In the description that follows, like components have been given the same reference numerals, regardless of whether they are shown in different examples. To illustrate example(s) in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

As used in the specification and claims, for the purposes of describing and defining the invention, the terms "about" and "substantially" are used to represent the inherent degree of uncertainty that may be attributed to any quantitative comparison, value, measurement, or other representation. The terms "about" and "substantially" are also used herein to represent the degree by which a quantitative representation may vary from a stated reference without resulting in a change in the basic function of the subject matter at issue. "Comprise," "include," and/or plural forms of each are open ended and include the listed parts and can include additional parts that are not listed. "And/or" is open-ended and includes one or more of the listed parts and combinations of the listed parts. Use of the terms "upper," "lower," "upwards," and the like is intended only to help in the clear description of the present disclosure and are not intended to limit the structure, positioning and/or operation of the disclosure in any manner.

Disclosed herein are a plurality of methods of tissue repair using at least two soft anchors that may be provided pre-attached to each other or may be coupled to each other during the procedure. At least some of the soft anchors are preferable provided or obtained with a knotless locking construct pre-assembled with the soft anchor. In some embodiments at least one of the soft anchors may include a pulley construct, defined further herein. In some embodiments the soft anchor may include both a pulley construct and a knotlessly locking construct.

An embodiment of a knotless locking soft anchor construct 100 is disclosed in FIG. 1A. This construct 100 and other knotless locking soft anchor constructs are disclosed in commonly owned U.S. Provisional application 63/275,491 filed Nov. 4, 2021; and U.S. Provisional Application 63/357,181 filed Jun. 30, 2022, and titled, "Knotless Soft Anchor System.", herein incorporated by reference in their entirety. FIG. 1A illustrates the knotless soft anchor construct 100 in a first configuration that is both undeployed and unlocked. Soft anchor 102 is a tubular braided body and a plurality of sutures (or equivalent flexible members) may be interwoven repeatedly through and along the sidewalls of the tubular body as shown. Tubular braided body of soft anchor is disclosed in more detail in at least commonly owned U.S. Pat. No. 9,962,149, titled "Tissue Repair Assembly"; commonly owned and herein incorporated by reference in its entirety. FIG. 1A schematically shows the construct 100, with a simplified representation of the anchor braided body 102, to show routing of the plurality of sutures therethrough. Construct 100 includes a soft tubular anchor 102, with a first suture 120 interwoven repeatedly through and along the anchor sidewalls. A second suture 130 may be fixedly coupled via a knot 132 at or close to an anchor distal end 116 and may interweave along and through the anchor 102 solely along a first side of the anchor longitudinal axis 106. The first suture 120 may extend within a cannulated length of the second suture 130, defining a spliced length or knotless locking length 137, the knotless locking length 137 coextensive with the anchor 102. The knotless locking length 137 may interweave repeatedly through the anchor 102 on a single side of the anchor longitudinal axis 106. Interweaving repeatedly preferably includes extending through the soft anchor sidewall at least three times, at axially spaced locations along the tubular braided body. In many construct embodiments four passes are shown beginning and ending with the flexible member within the lumen 105 of the tubular braided body. First suture 120 may operate as a deploying member and also as a transfer member and may therefore be removed from the anchor 102 and construct 100 in its final configuration. Second suture 130 may operate as a repair suture, as defined herein. Second suture 130 may remain in the construct 100 in its final, deployed, and knotless locked configuration. Construct 100, as well as other knotless locking constructs and operation thereof is disclosed in more detail in co-pending and commonly assigned U.S. provisional patent application, 63/275,491, titled "Knotless Soft Anchor System"; filed Nov. 4, 2021, herein incorporated by reference in its entirety.

Figure 1B:
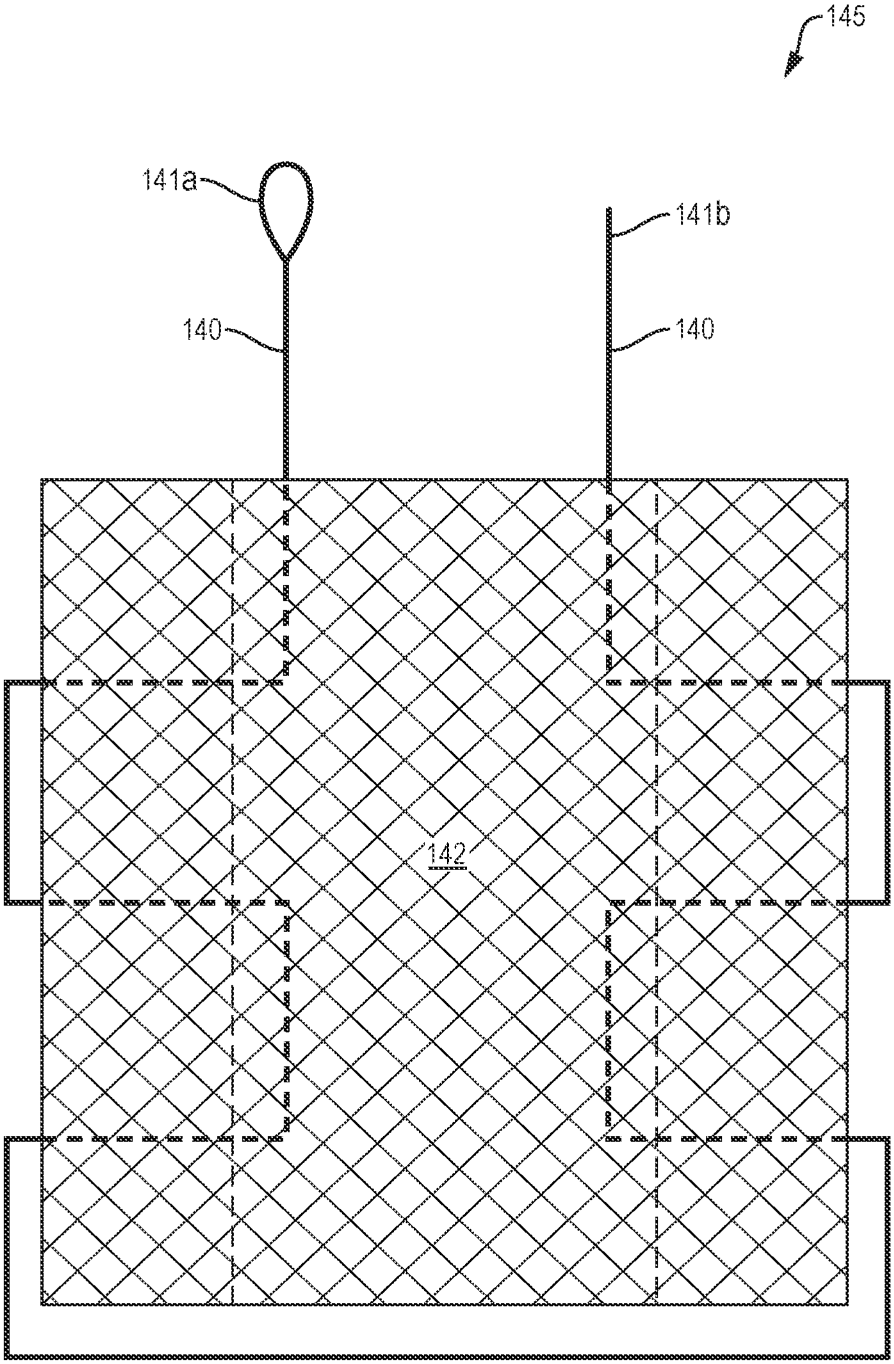
FIG. 1B illustrates a soft anchor pulley construct, in accordance with this disclosure.

FIG. 1B schematically shows a soft anchor pulley construct 145 that may include an anchor 142 with a suture 140 interwoven therethrough. Anchor 142 may be a tubular braided body similar to anchor 102. Construct 145 may be absent a knotless locking construct and may be similar to construct disclosed in at least U.S. Pat. No. 9,962,149, titled "Tissue Repair Assembly"; commonly owned and herein incorporated by reference in its entirety, with the exception that suture 140 may include a snaring end 141*a* configured to engage and snare a separate suture. Tension on ends 141*a* and 141*b* may deploy anchor 142 to anchor it within a bone hole. Tension on ends 141*a* and 141*b* may deploy anchor 142 to anchor it with an external surface of bone, soft tissue, or scaffold. With the separate suture snared, tension on end 141*b* may then shuttle this separate suture through the anchor 142. In some example embodiments more than one suture 140 may be interwoven through the tubular braided body, at adjacent or circumferentially offset locations, to provide more connecting and pulley links. This may be similar to the circumferentially offset routing illustrated in in FIG. 1C. Construct 145 may define an anchoring pulley construct, for reasons described later.

The separate suture may include a plurality of separate sutures, such that tensioning end 141*b* may shuttle the plurality of separate sutures through the anchor 142. The separate suture(s) may include a suture tape. As such, a smaller insertion instrument may be employed that is sized to house the anchor 142 and manage a relatively smaller sized suture 140, and upon deployment and removal of the insertion instrument, a separate suture that is larger in diameter may then be shuttled through the anchor 140. As such, construct 145 may advantageously provide a tissue anchor system with a minimal insertion instrument size, and thereby require a corresponding smaller skin incision and/or bone hole to be prepared, while subsequently allowing larger linking or repair sutures to couple to the anchor 142.

Figure 1C:
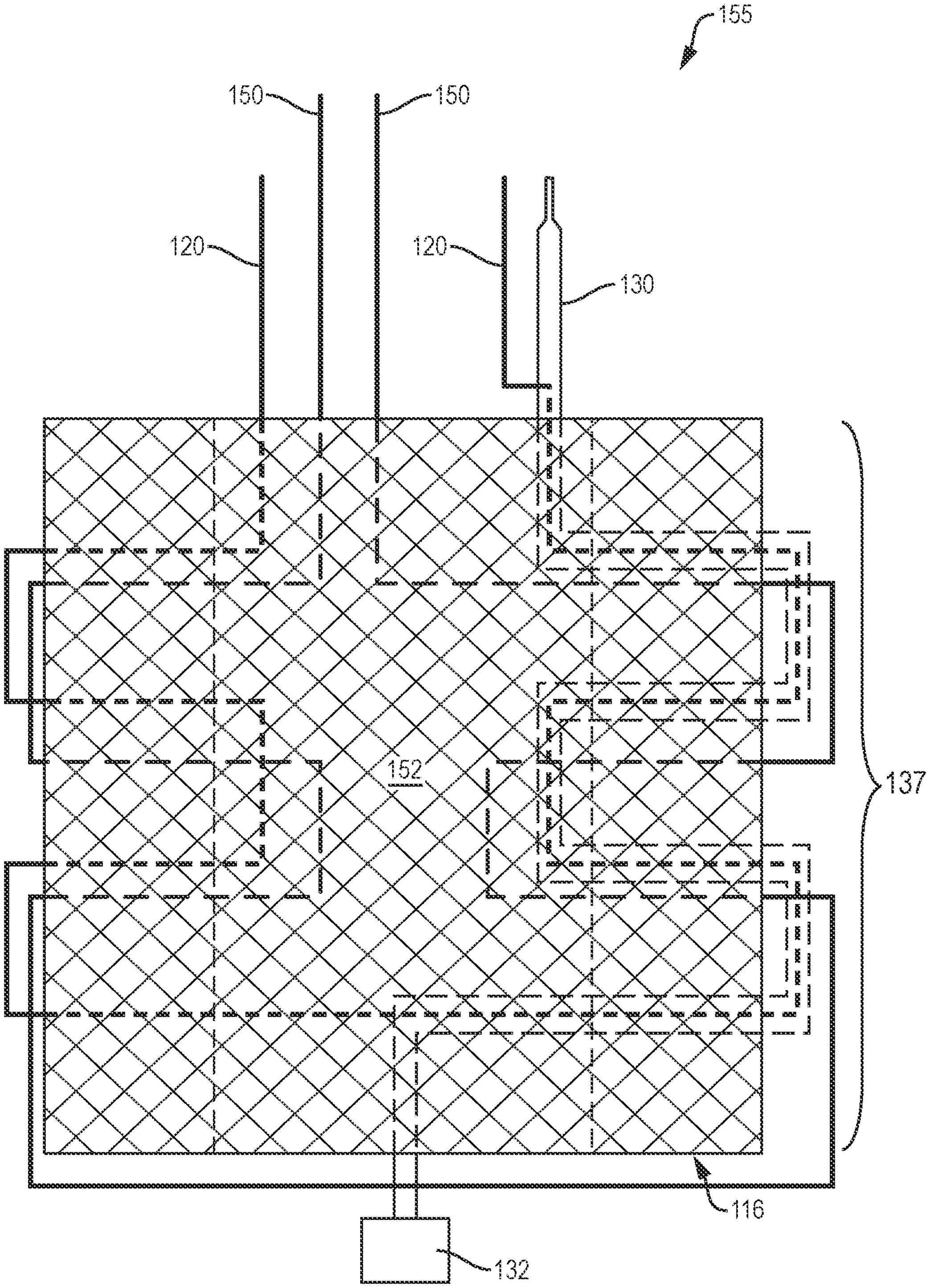
FIG. 1C illustrates a soft anchor combination pulley and knotless construct, in accordance with this disclosure.

FIG. 1C schematically shows a further example construct 155 that includes an anchor 152 with a knotless locking construct interwoven therethrough, similar to construct 100, with at least one additional suture 150 (or equivalent flexible member) coupled thereto. The additional suture 150 may be free of the second suture cannulation and may provide a pulley means, similar to suture 140. Additional suture 150 may interweave along anchor 152, in a similar path to other suture paths disclosed herein. Additional suture 150 may interweave along anchor 152 along a path that is circumferentially offset from the sutures 120 and 130. Construct 155 is defined as a combination knotless locking and pulley construct.

Member 120 or 140 may be a polyester size #0 suture. In some embodiments, the member 120 may be a spliced loop construct with a splice length that extends through the assembled anchor and at least through a locking passage entrance to limit forces required to shuttle the repair suture through any working openings, such as for example through the locking passage 137. A transfer member construct is disclosed in co-pending U.S. provisional application Ser. No. 63/317,671 filed Mar. 8, 2022, titled "Smooth Transfer Suture Loop"; and U.S. provisional application Ser. No. 63/342,843 filed May 17, 2022, titled "Transfer Suture Loop", both incorporated by reference in their entirety.

Figure 1D:
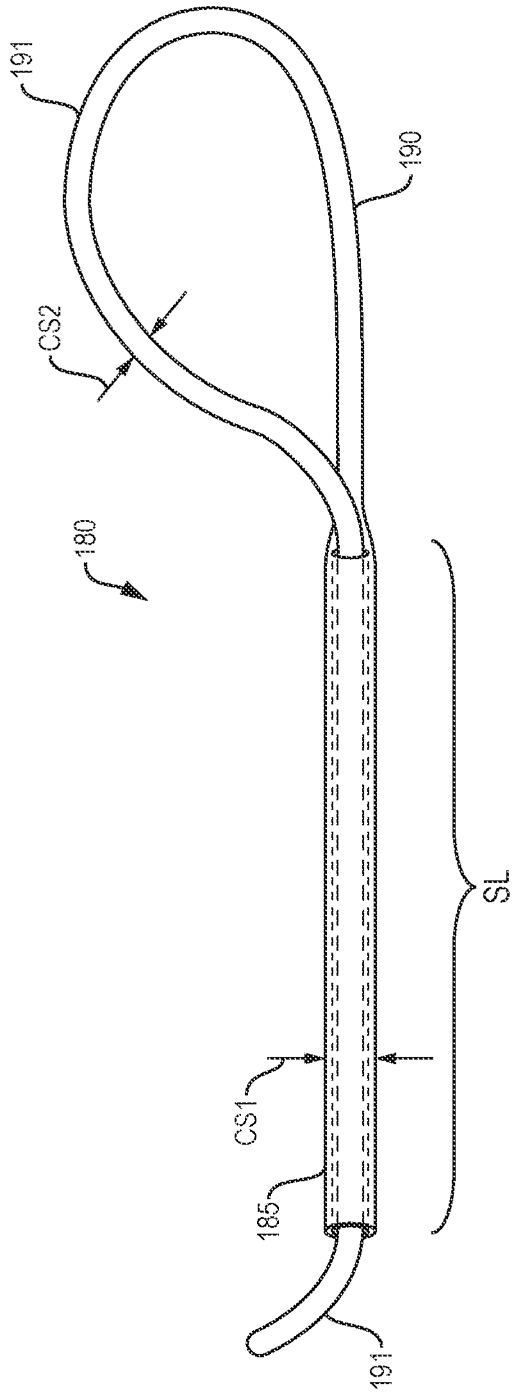
FIG. 1D illustrates a transfer suture construct, in accordance with this disclosure.

Transfer member construct 180 is schematically shown in FIG. 1D and may include a braided body that may be include two length portions 185 and 190 that may be different from each other. First length portion 185 may be cannulated and may define a first cross section CS1 substantially therealong. First length portion 185 may be formed with a first number of braided strands, that may be between 8-32. Second length portion 190 may be smaller in cross section (CS2) substantially therealong and may include strands braided through its core and therefore may not have a longitudinal passage therealong. Second length portion 190 may be formed with a second number of braided strands, that may be between 8-32. First length portion 185 may have a greater number of braided strands than the second length portion 190. In some embodiments, first length portion 185 may include 16 strands and second length portion 190 may include 8 strands. First cross section CS1 may be larger than second cross section CS2. First length portion 185 may be similar to size #2 suture, while second length portion 190 may be similar to size 2.0 suture.

More detail, including formation of construct 180 may be found in the co-pending applications listed. The transfer member construct 180 includes a looped end 191 that may be the loop at the suture snare end 122*a*, with reference to FIGS. 1A and 1C. Looped end 191 may be a static loop. Looped end 191 may be formed entirely of the second length portion 190 to reduce the cross section of the loop end as it is collapsed to be drawn through the corresponding anchor (102 142, 152) and locking passage portion 137. Second length portion 190 may define a spliced loop 191, such that the second length portion extends along cannulation of first length portion 185 for a length defining a splice length SL. Splice length SL has a length that preferably extends through all working openings on the system, including at least a portion of the locking passage portion 137. Therefore, locking passage portion 137 interweaves through the anchor, and may contain a spliced length SL of the transfer member construct 180 therethrough also, such that three coaxially arranged braided bodies interweave along a single sidewall of the anchor 102, the three bodies including the repair suture 130, the transfer member first portion 185 and the transfer member second portion 190. In some embodiments, given that the transfer member 180 is also at least a portion of the deploying member and given that the spliced length SL has been found to increase the overall strength of the deploying member, the splice length SL may have a length such that two opposing ends of splice length SL are operatively coupled to a deployment actuation engagement means of an insertion instrument, such that higher tensioning loads may be applied to the deployment/transfer member which may result in a high anchor fixation strength.

Repair of tissue or augmentation of a primary repair may include forming a multi-anchor suture staple or multi-anchor link, employing at least two constructs that may include combinations of constructs 100, 145 and 155. Each anchor of the corresponding construct may be deployed to fix the anchor relative to target tissue and then links may be formed between the anchors. Specific embodiments of linked constructs and a method of linking are now described.

Figure 2A:
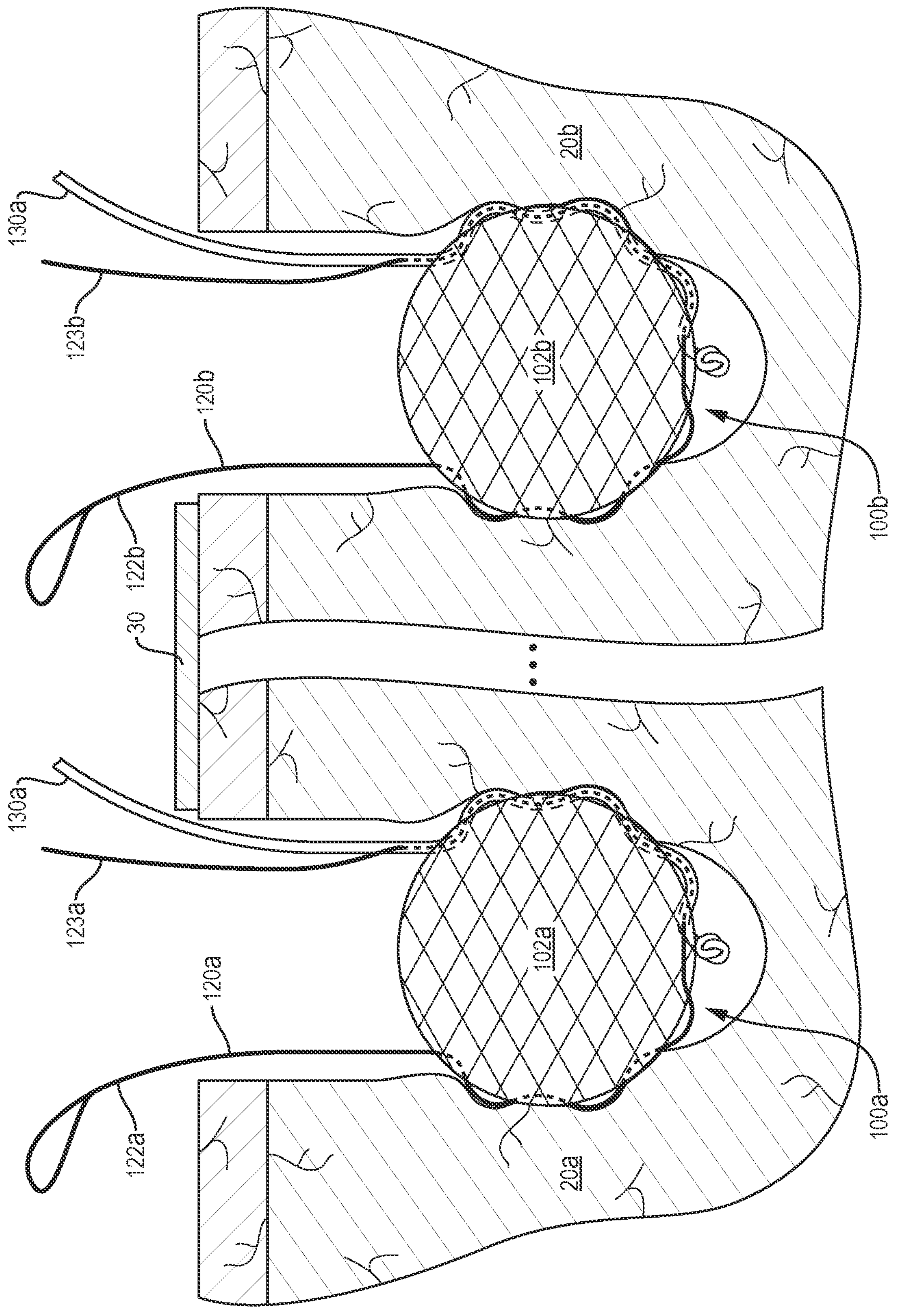
FIGS. 2A-2D illustrate the steps for forming a knotless soft anchor staple construct, in accordance with this disclosure.
Figure 2B:
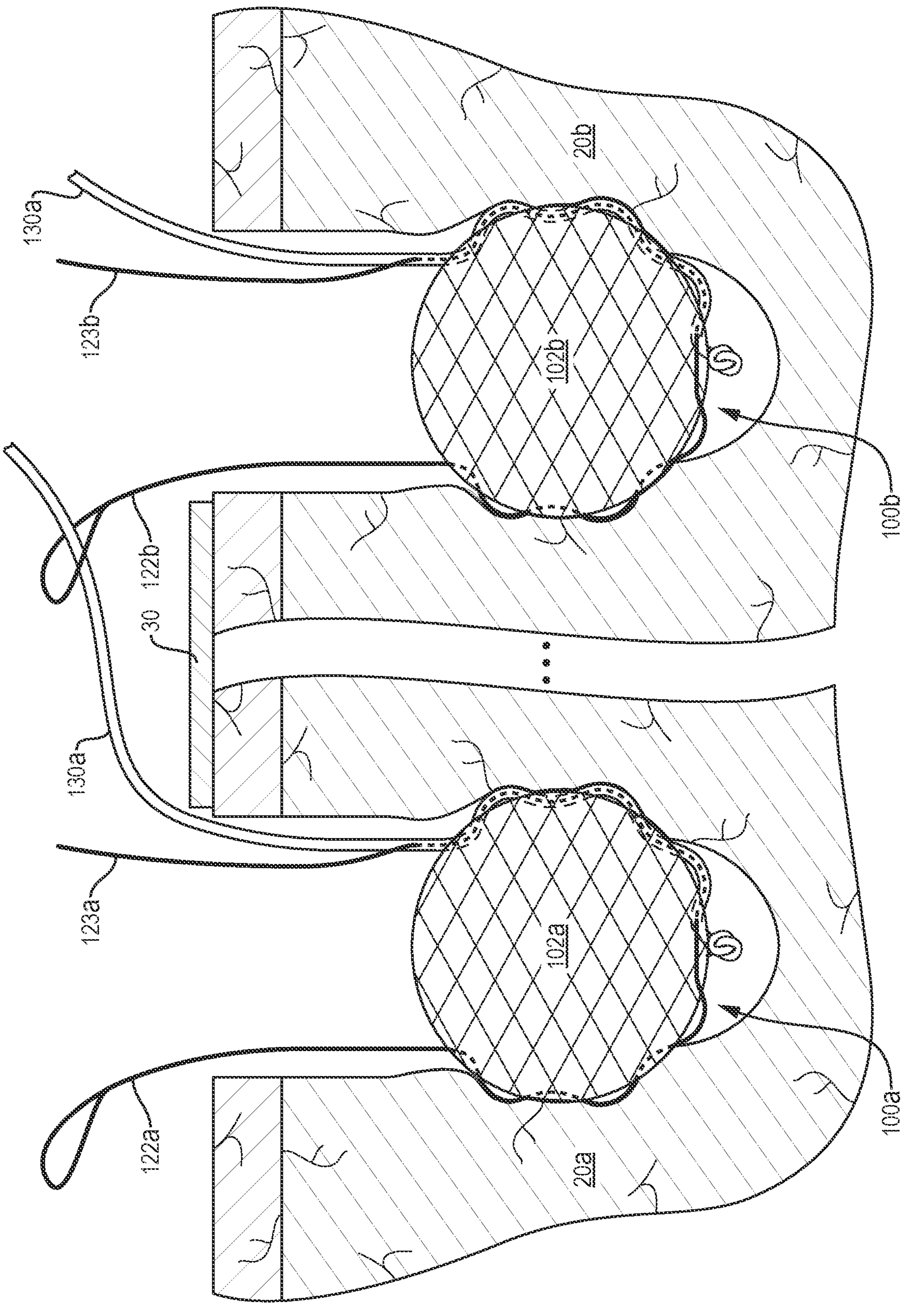
Figure 2C:
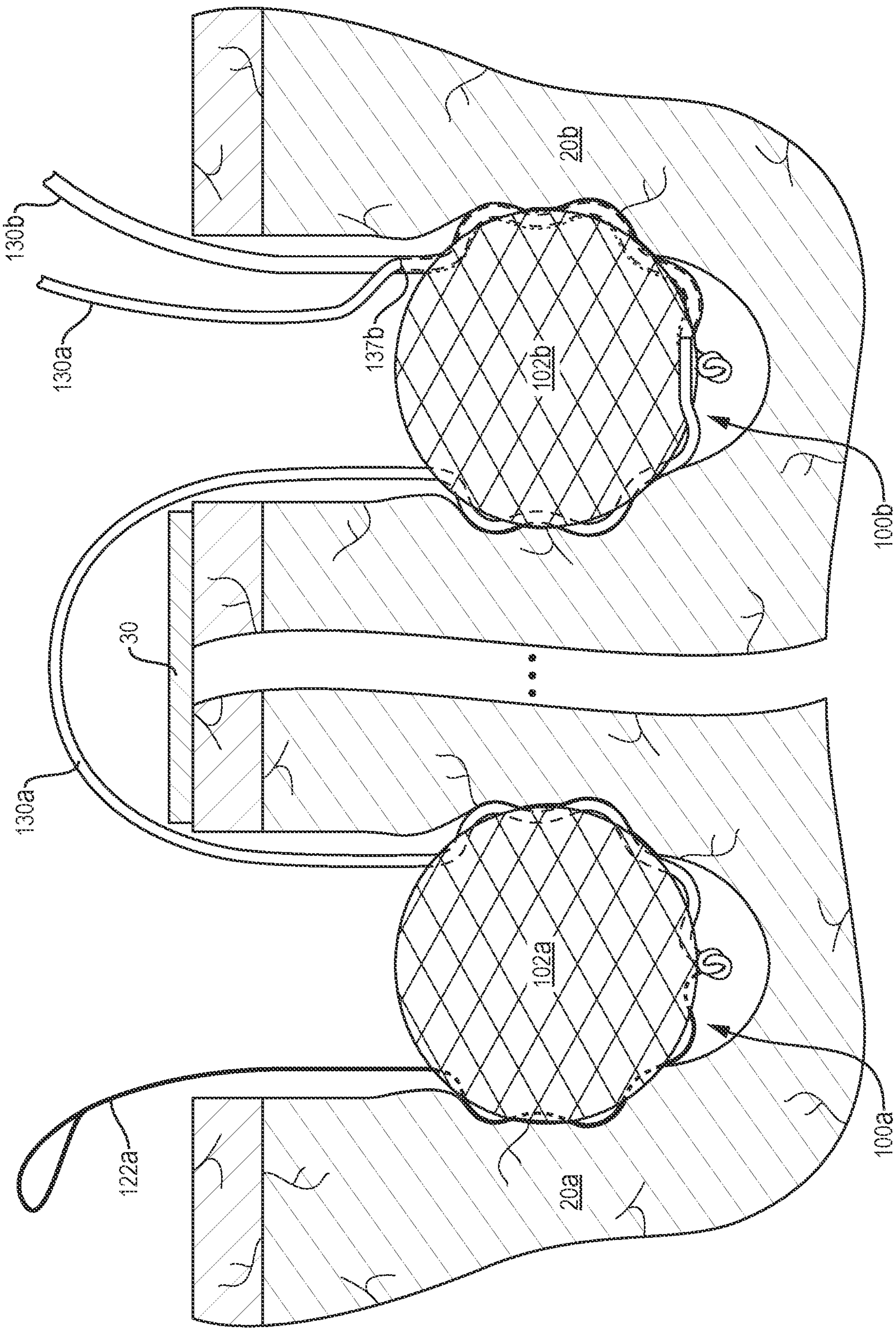

A first example link, and method of forming is shown in FIG. 2A-2D. This link may be used to re-attach a tissue to a bone, augment a primary ligament repair or attach a scaffold, sheet-like implant, or graft to a target tissue. This link may be a knotless all-suture staple and includes two soft anchor knotless anchor constructs such as construct 100, differentiated over each other by the label 100*a* and 100*b*. Each construct 100*a*, 100*b* may be substantially the same as construct 100, including a soft anchor (102*a*, 102*b*). Soft anchors 102*a*, 102*b* advantageously form a strong fixation within or with tissue when deployed. Shown in FIG. 2A, are the two anchors 102*a*, 102*b* in a deployed configuration, to set the anchors 102*a*, 102*b* in their respective tissue cavities. These cavities may be prepared bone holes, that may extend all the way through the bone or have a blind end (as illustrated). These cavities may be through different portions of the same bone, or through different bones. Each anchor 102*a*, 102*b* may be separately deployed via their own dedicated insertion instrument. Insertion instruments are disclosed in commonly owned U.S. Pat. No. 10,905,409, and commonly owned co-pending patent application with an internal title PT-5834-WO-PCT, both incorporated by reference in their entirety. Tension applied to at least on one of the proximally extending members (120*a*, 130*a*) may deploy the anchor 102*a*, as illustrated in FIG. 1A. Repair suture 130*a* may act as a deploying member. In some embodiments, tension may be applied to all proximally extending limbs (122*a*, 123*a*, 130*a*) to deploy the anchor 102*a* to a laterally expanded form. This bunches up the anchor 102*a*, as shown, changing the tubular body to a deployed configuration and fixes the anchor 102*a* within the target tissue 20*a*. First anchor 102*a* may be inserted and deployed within or on a first tissue 20*a* on a first side of a tissue repair. An example repair tissue 30 is illustrated in FIG. 2A-2D.

A second knotless anchor construct 100*b* may be the same as first knotless anchor construct 100*a* and be deployed in the same manner. Second construct 100*b* may be independently inserted into a second tissue 20*b* adjacent repair tissue 30. Second construct 100*b* may be coupled to the second tissue 20*b* on an opposing side of the repair tissue 30. Second tissue 20*b* may be a different portion of the first tissue 20*a*. In some embodiments, first tissue 20*a* may be a first bone, and the second tissue 20*b* may be a second bone.

As illustrated in FIG. 2A, two knotless constructs 100*a*, 100*b* may be inserted into tissue(s) either side of a repair tissue 30. In some embodiments, the constructs 100*a*, 100*b* may be inserted through repair tissues or grafts or implant, such that these repair tissues, grafts, or implants cover at least one of the anchors 102*a*, 102*b*. Both constructs 100*a*, 100*b* may be provided separate from each other and have their own dedicated insertion instruments. While in other embodiments, both construct 100*a*, 100*b* may be provided in separate portions of a single insertion instrument, inserting the constructs 100*a*, 100*b* while detached from each other may allow for flexibility in location of the two anchor constructs 100*a*, 100*b*. Both constructs 100*a*, 100*b* may be separately deployed, to anchor each construct within the tissue (20*a*, 20*a*). For example, the first construct 100*a* may first be inserted into tissue and deployed, before inserting and deploying the second construct 100*b*.

Figure 2D:
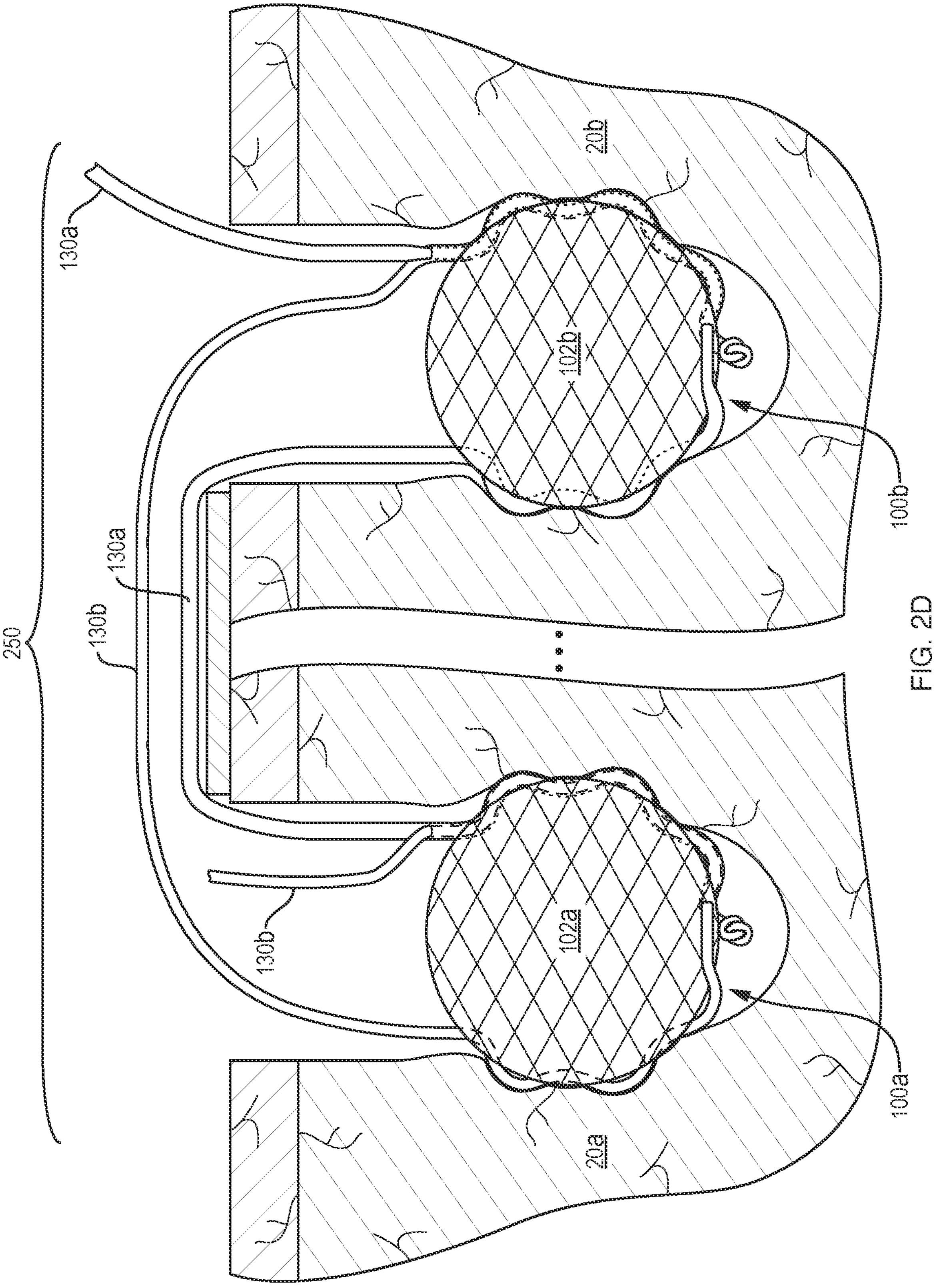

To form the staple construct 250, illustrated in FIG. 2D, repair suture 130*a* of first construct 100*a* may be snared or coupled to member 120*b* of second construct 100*b*. Member 120*b* may include a snaring end 122*b* to receive repair suture 130*a* therethrough before shuttling repair suture 130*a* through second anchor 100*b* and cannulation (suture locking passage) 137*b*. Illustrated in FIG. 2C, withdrawing the member 120*b* of the second construct 100*b* transfers the repair suture 130*a* through and along the second knotless anchor 102*b*, therefore member 120*b* is both a deploying member and a transfer member. Member 120*b* may be formed as a transfer member construct 180 as disclosed herein. Withdrawing member 120*b* removes it from the second construct 100*b*. Withdrawing the member 120*b* transfers the repair suture 130*a* of the first construct 100*a* through and along cannulation 137*b* of the second knotless anchor construct 100*b*. Repair suture 130*b* of the second construct 100*b* may then be snared or coupled to member snare end 122*a* of first construct 100*a* and drawn through first construct 100*a*, to form a second link or bridge between the two constructs 100*a*, 100*b*, thereby forming knotless all-suture staple 250, illustrated in FIG. 2D. Tension on ends 130*a*, 130*b* may attach the repair tissue 30 and also knotlessly lock the knotless all-suture staple 250 in two locations.

In some example methods the suture staple may be placed over a ligament repair, such as for example an Anterior Talofibular Ligament (ATFL) that has been repaired and the suture staple construct 250 may augment the repair. In some example methods the suture staple may couple a sheet-like implant, scaffold, or graft to a tissue.

Figure 3:
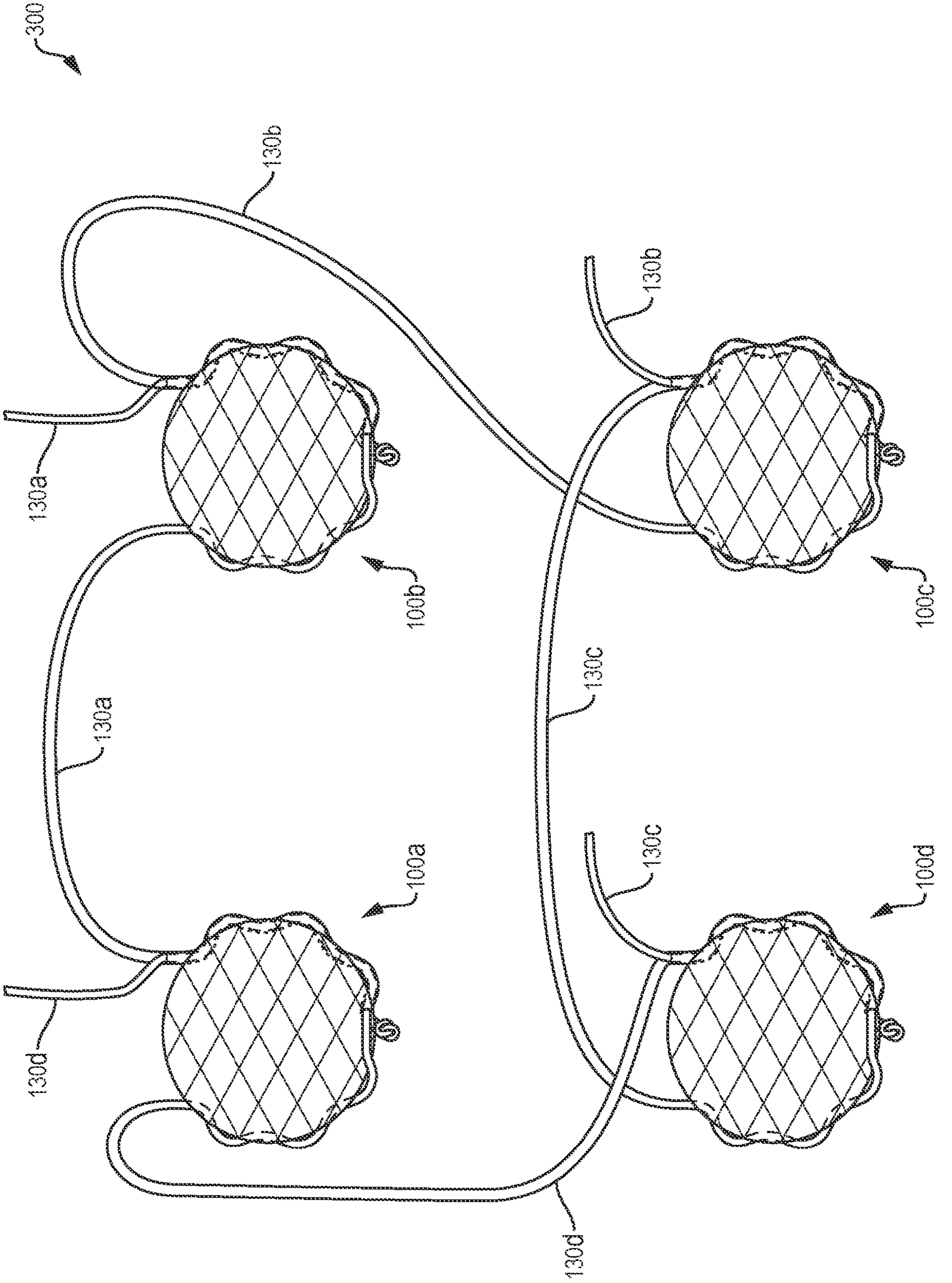
FIG. 3 illustrates a chain knotless soft anchor construct, in accordance with this disclosure.

FIG. 3 illustrates an all-suture knotless chain 300 in its final, knotlessly anchored form. This is formed similarly to the steps illustrated in FIG. 2A-2C, at which point rather than forming a double bridge over the tissue 30, further anchors may be inserted, and a chain may be formed, by transferring and coupling repair sutures through the other knotless anchors. An example of this is shown in FIG. 3 that includes four knotless constructs, designated 100*a*, 100*b*, 100*c* and 100*d* to differentiate each construct. Any number of knotless constructs may be used. The anchors may be arranged according to the target repair. The anchors (102*a*, 102*b*, 102*c*, 102*d* . . . ) are shown arranged in a simplified quadrilateral, for ease of understanding, but may be arranged according to the repair or graft/scaffold that is being attached. Each construct 100*a*, 100*b*, 100*c* and 100*d* may be separately inserted and deployed within or on a tissue. Each repair suture 130*a*, 130*b*, 130*c*, 130*d* may be snared through an adjacent anchor construct in a daisy chain style, as shown. For example, repair suture 130*a* of first anchor construct 100*a* is transferred across and through second anchor construct 100*b*. Repair suture 130*b* of second anchor construct 100*b* may be transferred across and through third construct 1010*c* and so on. A complete loop may be formed by the links formed by the repair sutures. In other embodiments the chain may cross over each other, for example the sequential path, with reference to FIG. 3 may start with repair suture 130*a* transferred over to and coupled directly to construct 100*c*, and repair suture 130*c* transferred over to and coupled directly to anchor construct 100*b*, and repair suture 130*b* transferred over to and coupled directly to anchor construct

100*d* and repair suture 130*d* transferred over to and coupled directly to anchor construct 100*a*. This may form a cross-over chain. This may strengthen the repair along preferred vectors. Another embodiment may include transferring two repair sutures from two different anchor constructs through a single third anchor construct, forming a Y-shaped repair.

Figure 4A:
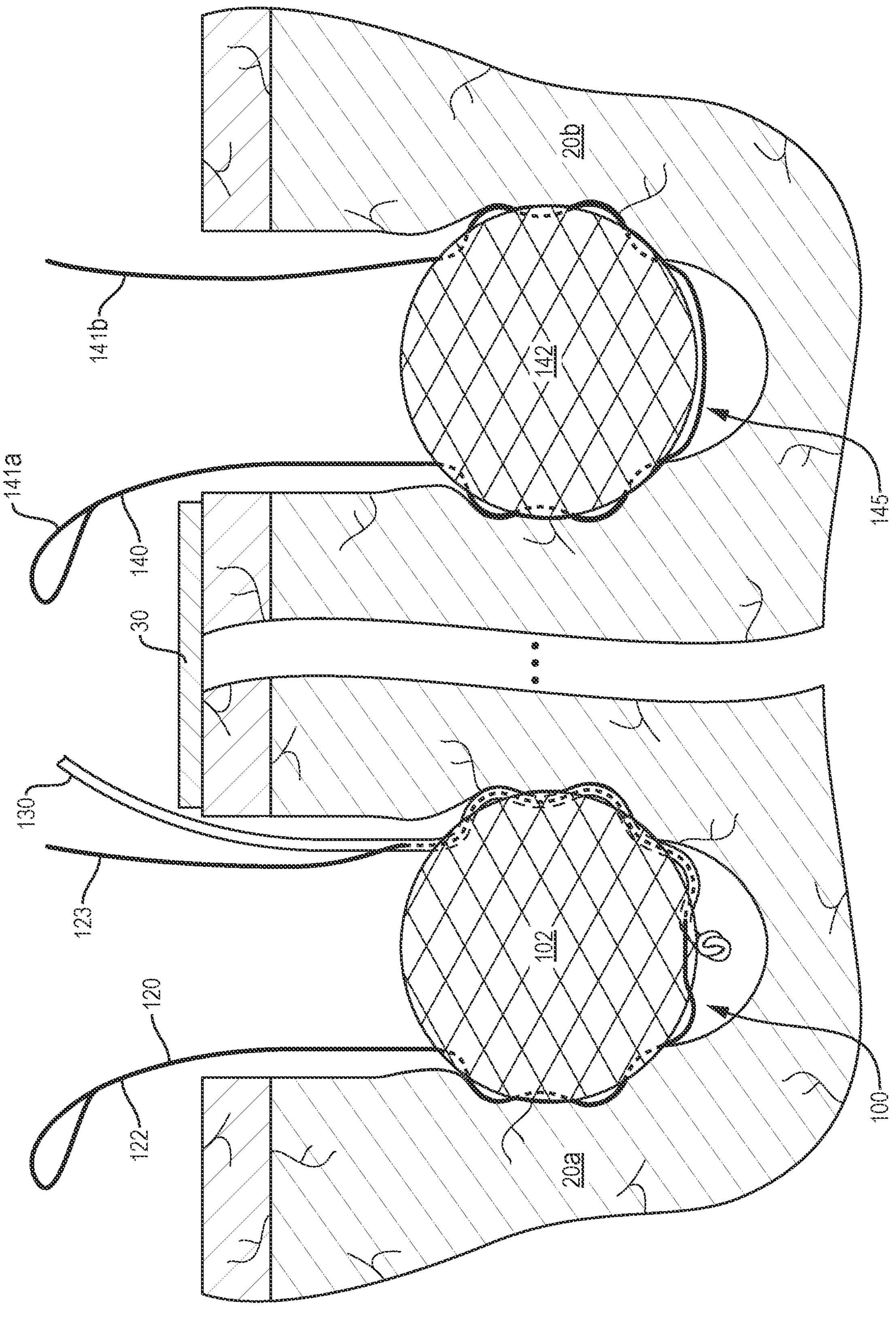
FIGS. 4A-4D illustrate formation of a knotless soft anchor linking construct, in accordance with this disclosure.
Figure 4B:
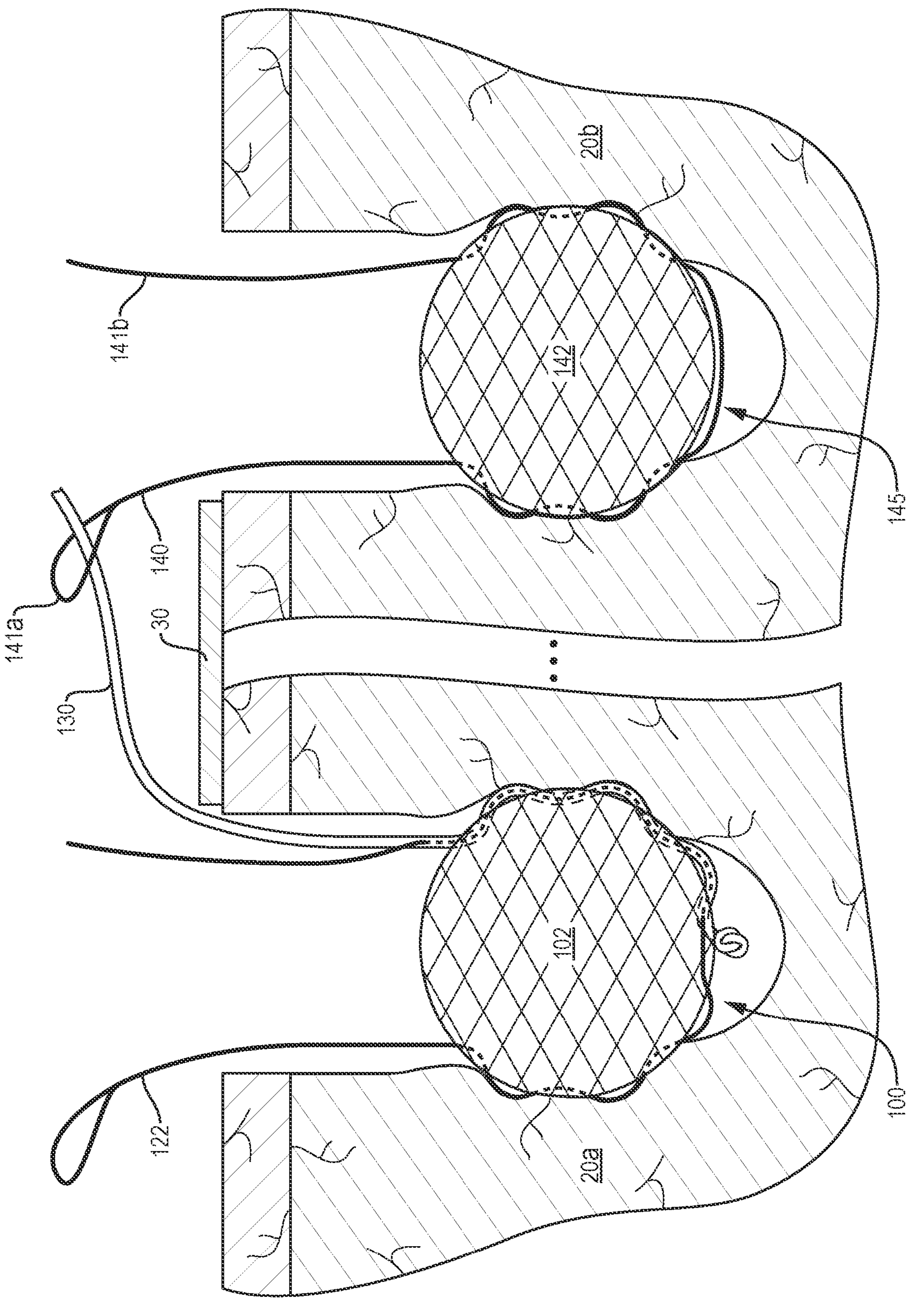
Figure 4C:
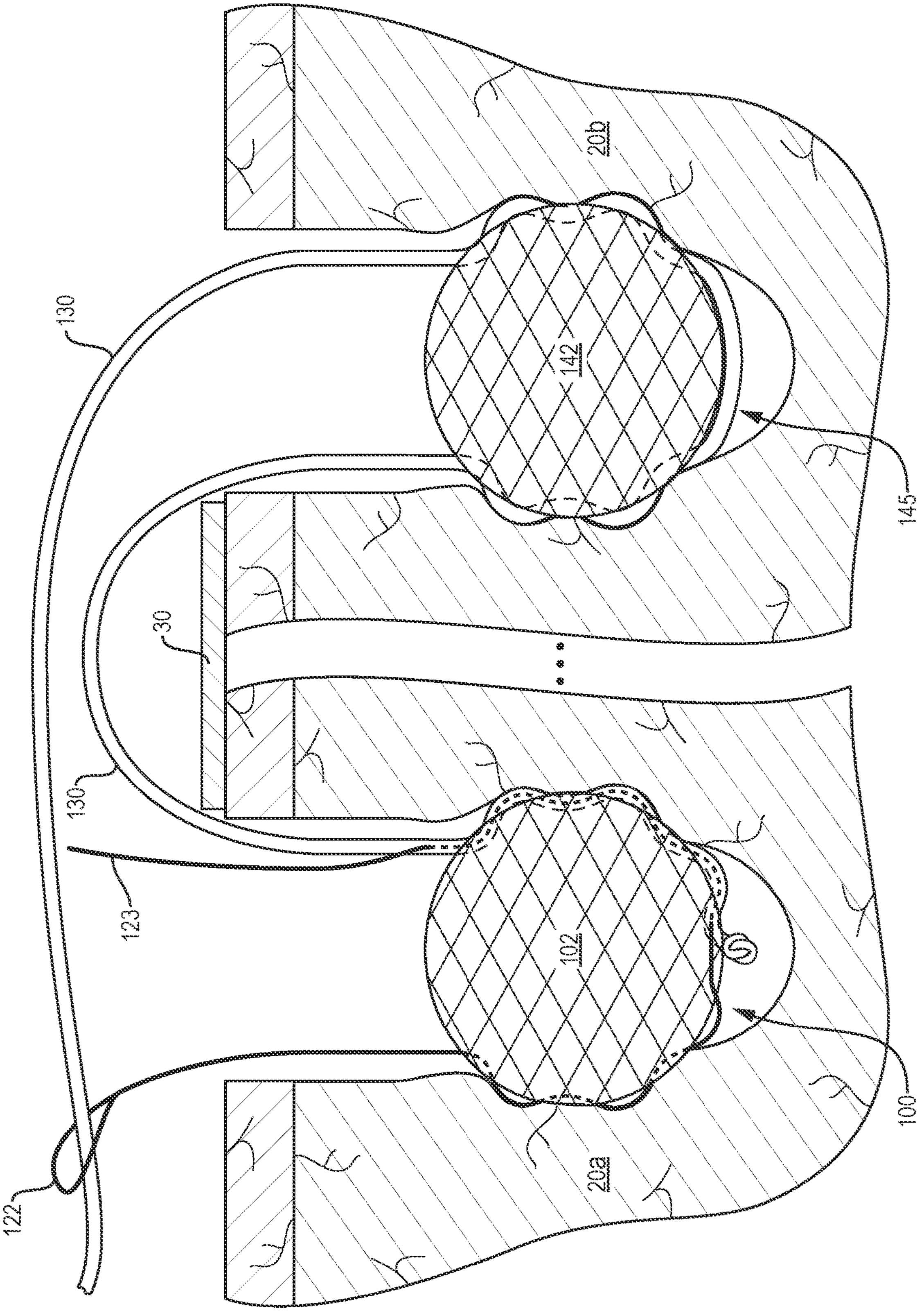
Figure 4D:
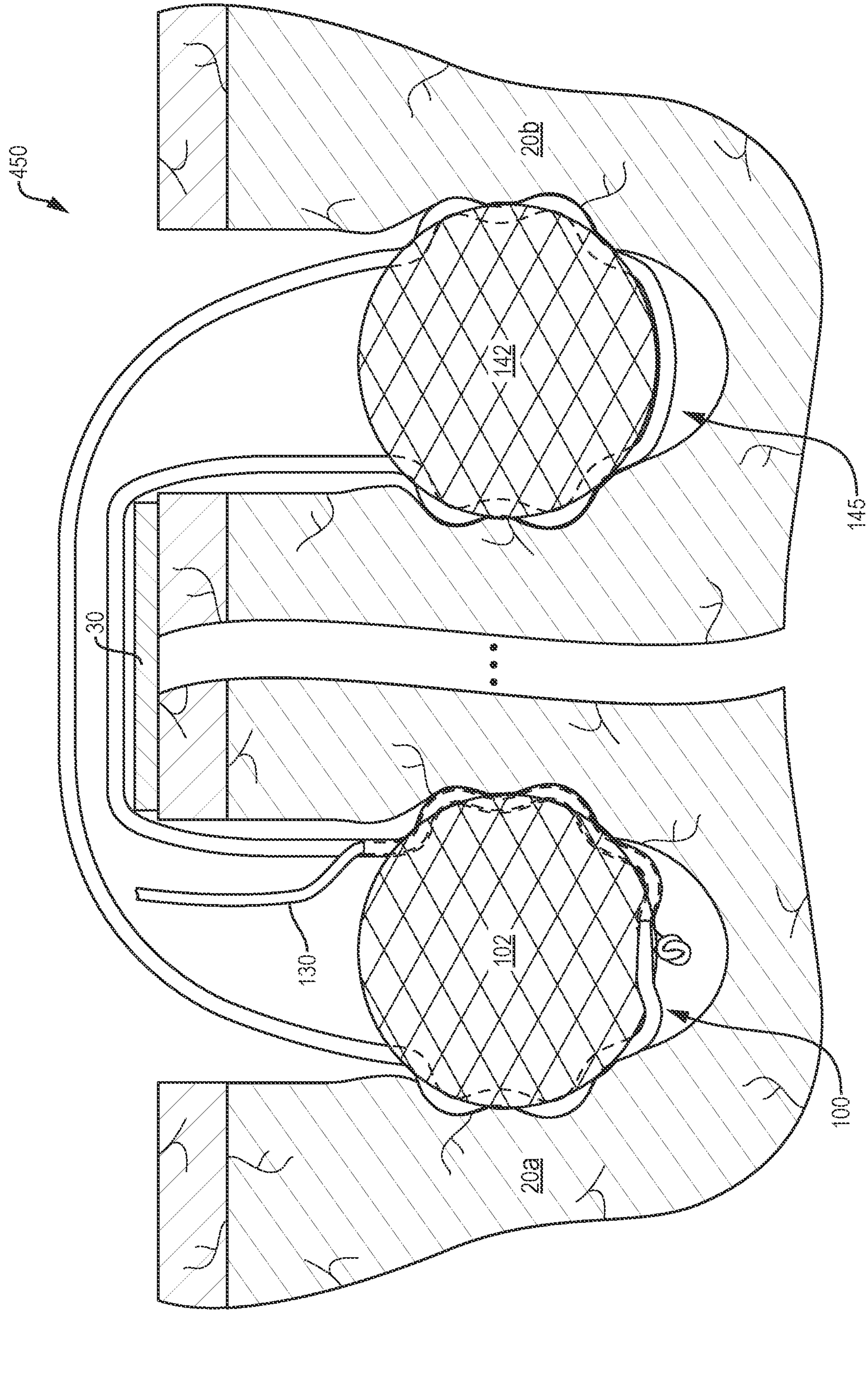
Figure 4E:
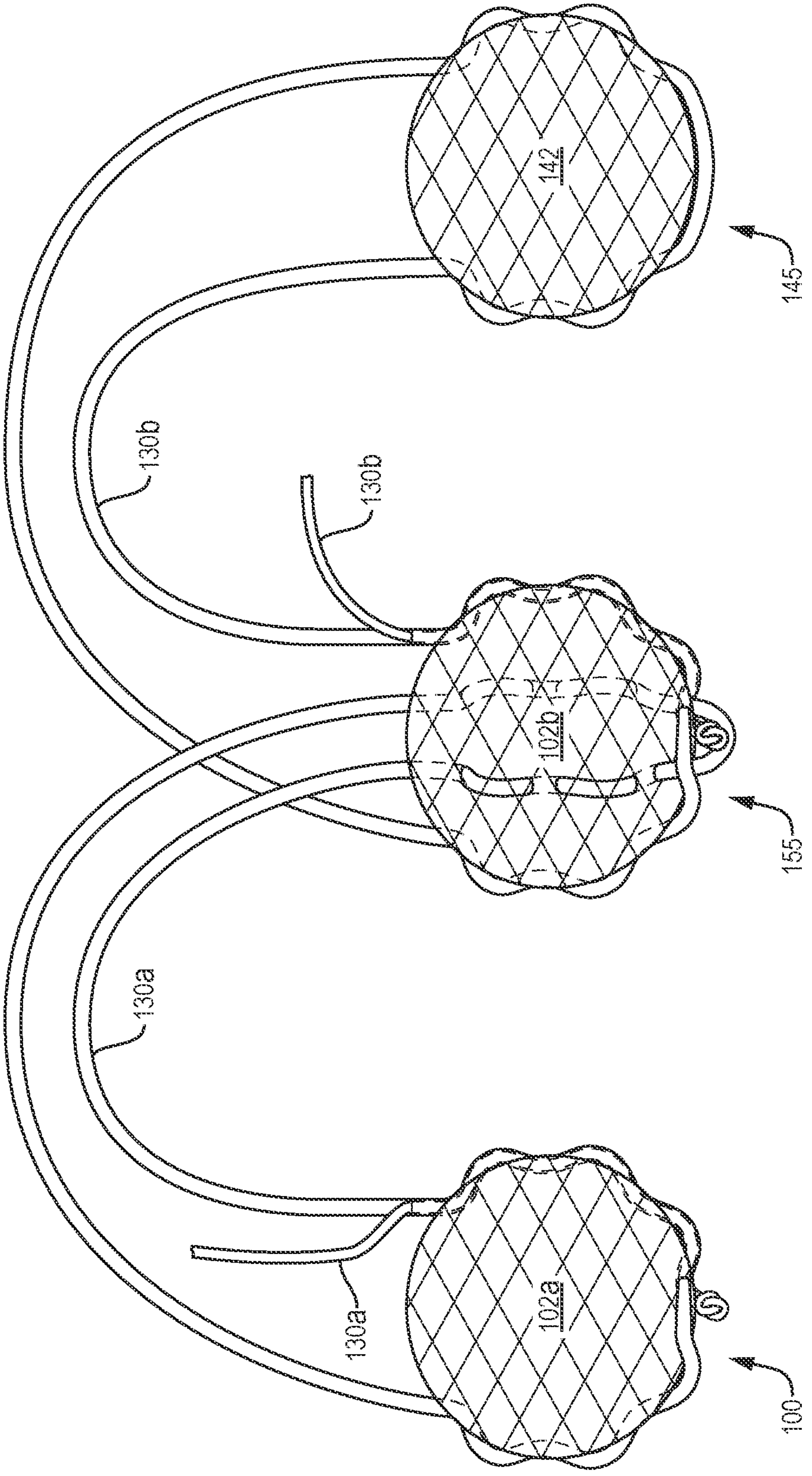
FIG. 4E illustrates a triple knotless soft anchor linking construct, in accordance with this disclosure.

Another example link and method of forming are shown in FIGS. 4A-4D. This link may be used to re-attach a tissue to a bone, augment a primary ligament repair or attached a scaffold or graft to a target tissue. This link may be a simple bridge and may include two soft anchors, one a knotless anchor constructs 100 and the other may be a pulley anchor construct 145. Shown in FIG. 4A, the two anchors 102, 142 are shown deployed within their respective tissue cavities. These cavities may be prepared bone holes, that may extend all the way through the bone or have a blind end. In other example, anchors 102, 142 may be deployed to engage outer portions of bone or tissue, the link may extend through corresponding tunnels of each tissue. Similar to the example method of forming the staple construct 250, each anchor 102, 142 may be separately deployed via their own dedicated insertion instrument. Tension applied to member 120 (which may transfer member construct 180) may deploy the anchor 102, as illustrated in FIG. 4A. Tension may be applied to all proximally extending limbs 122, 123 and 130 to deploy anchor 102. Tension applied to member 140 may deploy anchor 142. Tension acts to bunch up the corresponding anchor 102, 142, changing the tubular body to a deployed configuration and fixes the anchor 102, 142 within the corresponding target tissue 20*a*, 20*b*.

As illustrated in FIG. 4A, both constructs 100, 145 may be inserted into tissue(s) either side of a repair tissue 30. In other examples, construct 100, 145 may be disposed through a repair tissue or graft/implant. To form the linking or bridging construct 450, illustrated in FIG. 4D, the deploying member 140 now changes roles to become a transfer member. Repair suture 130 of construct 100 may be coupled to transfer member 140 of construct 145. Member 140 may include a snaring end 141*a* to receive repair suture 130 therethrough (FIG. 4B) and then shuttle repair suture 130 through second anchor 142. Illustrated in FIG. 4C, withdrawing the member 140 of the second construct 145 transfers the repair suture 130 through and along the anchor 142. Withdrawing member 140 removes it from the construct 145. Repair suture 130 may then be snared or coupled to transfer snare end 122 and drawn through construct 100, to form a second link or bridge between the two constructs 100, 145 and through knotless locking passage 137. A link is therefore formed with a single length of repair suture that passes through pulley anchor 142 and back again through soft anchor knotless construct 100. Tension on end 130 may attach the example repair tissue 30 and also knotless lock the knotless all-suture linking construct 450.

In some example methods the suture bridge 450 may be placed over a ligament repair, such as for example an Anterior Talofibular Ligament (ATFL) that has been repaired and the suture staple construct 150 may augment the repair. In some example methods the suture bridge 450 may couple a scaffold or graft to a tissue.

Another example methods of repair may include three anchors, including three different constructs, the soft anchor knotlessly locking construct 100, the pulley construct 145 and the combination construct 155. A final coupled embodiment is shown, where repair suture 130*a* from construct 100 is interwoven, via shuttle member 150 (not shown) through anchor 102*b* and then back to anchor 102*a*, forming a first linking bridge similar to bridge 450. Also shown is second link wherein repair suture 130*b*, fixedly coupled to anchor 102*b* extends over to anchor 142 and is shuttled through anchor 142 (via member 140) through anchor 142 and then back through anchor 102*b*. The bones and repair are omitted from this drawing, for simplicity.

The inventors envision many optional links between two of more soft anchors. Examples of links are shown in FIGS. 5A-5G, in simplified form.

Figure 5A:
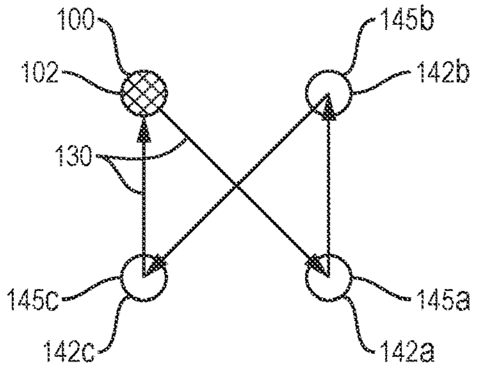
FIGS. 5A-5G schematically shows other example multi-anchor linking constructs, in accordance with this disclosure.

FIG. 5A schematically shows a cross over arrangement of a plurality of constructs (100, 145*a*, 145*b*, 145*c*). Constructs 145*a*, 145*b* 145*c* may be three pulley constructs 145, that may be placed in spaced apart portions of the same tissue or in different tissues. In this arrangement, a repair suture 130 originates at construct 100 and then is sequentially shuttled through constructs 145*a*, then 145*b*, then 145*c*, via shuttle members similar to member 140. These links may be preferably formed with the anchors already deployed via tension from at least the corresponding deploying member as discussed earlier. Repair suture 130 may terminate back at the origination anchor, 102 of construct 100, drawn through via member 120 (or transfer member construct 180) through suture locking passage 137. Tensioning end of repair suture 130 may knotlessly lock the repair suture 130 from sliding further. Tensioning end of repair suture 130 may knotlessly lock the repair suture 130 within the arranged anchors (102, 142*a*, 142*b*, 142*c*).

Figure 5B:
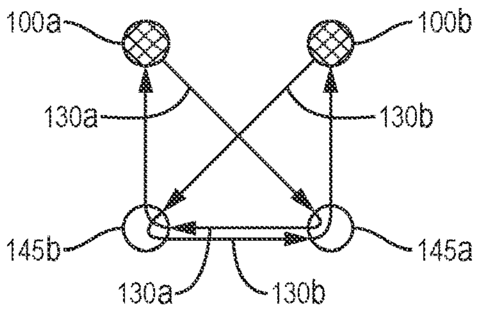
Figure 5C:
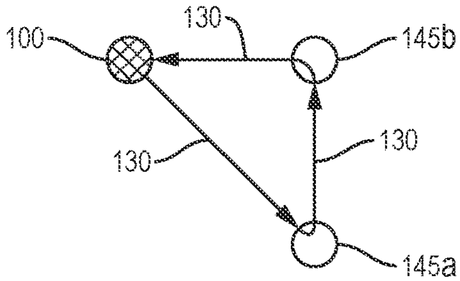
Figure 5D:
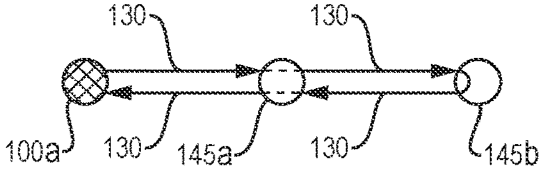
Figure 5E:
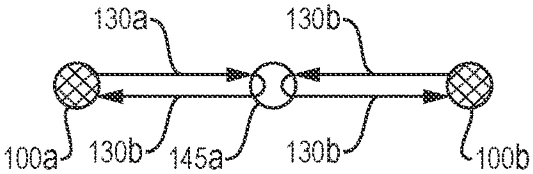

FIG. 5B schematically shows another cross over arrangement of a plurality of constructs including two soft anchor knotless constructs (100*a*, 100*b*) and two pulley constructs 145*a*, 145*b*. In this embodiment, constructs 145*a*, 145*b* may have two transfer members each, to draw both repair sutures 130*a*, 130*b* therethrough. Two knotlessly locked loops may be formed, with a double link between the two pulley constructs 145*a*, 145*b*. This may be a beneficial arrangement during repair of a rotator cuff or Achilles. FIG. 5C illustrates a triangular arrangement wherein the repair suture 130 is drawn through pulley construct 145*a* first, then pulley construct 145*b* before returning to construct 100 to knotlessly lock the arrangement. The arrangement shown in FIG. 5C may be applicable when coupling three separate bones of a patient joint, for a repair or repair augmentation. Arrangement shown in FIG. 5C is one of the loops shown in FIG. 5B. FIG. 5D schematically shows an arrangement wherein the repair suture 130 is first drawn through construct 145*a*, then through 145*b* before returning to construct 145*a* and then back to original knotlessly locking construct 100. Construct 145*a* preferably includes two separate members (such as two members 140) to shuttle the repair suture 130 therethrough twice. FIG. 5E schematically shows an arrangement with two knotlessly locking constructs 100*a*, 100*b*, which may increase the locking strength of the multi-anchor arrangement relative to the arrangement shown in FIG. 5D. Construct 100*a* may knotlessly lock the repair suture 130*a* and construct 100*b* may knotlessly lock with repair suture 130*b*. In the arrangements, both repair sutures 130*a*, 130*b* may be draw through construct 145 simultaneously, (loop 141*a* may snare both repair sutures 130*a*, 130*b* at the same time, therefore only requiring a single transfer member 140.)

Figure 5F:
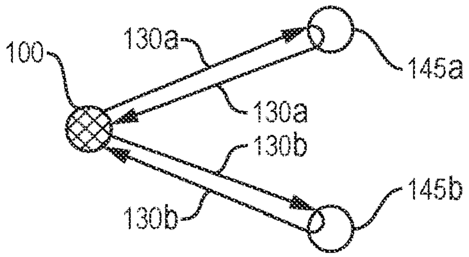
Figure 5G:
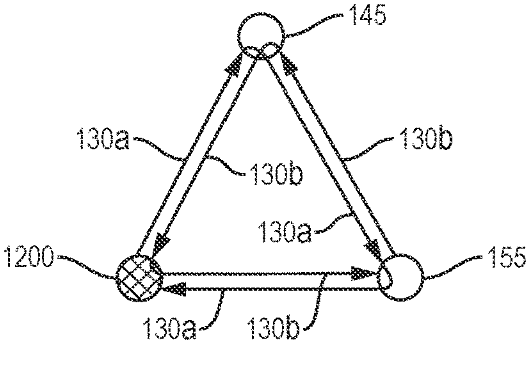

FIG. 5F schematically shows an arrangement with construct 100 that may be provided with two repair sutures fixed to and interwoven therethrough and two transfers members, one for each locking passage of the repair suture. This allows a first bridge connection (450) to construct 145*a* and a second independent bridge connection (450) to construct 1455*b*. Independently may mean independently connected and independently tensioned and locking. FIG. 5G illustrates a triangular arrangement with a construct 100, construct 145 and construct 155. Construct 100 may have double the repair constructs/transfer suture constructs as provided, similar to that shown in FIG. 5F. Construct 145 may have two members 140 to transfer each repair suture 130*a*, 130*b* separately, or may transfer repair sutures 130*a*, 130*b* simultaneously. Two parallel triangular arranged looped links bridge connections may be made, with two knotless locking constructs.

Non-limiting examples include repair of a rotator cuff, including a partially torn supraspinatus, AC joint, Achilles, Biceps Tenodesis, the elbow joint, thumb joints or repair of the Gluteus Medius. Other non-limiting examples include ACL Repair, ATFL Repair and augmentation, All inside meniscal root repair or MPFL reconstruction.

Figure 6B:
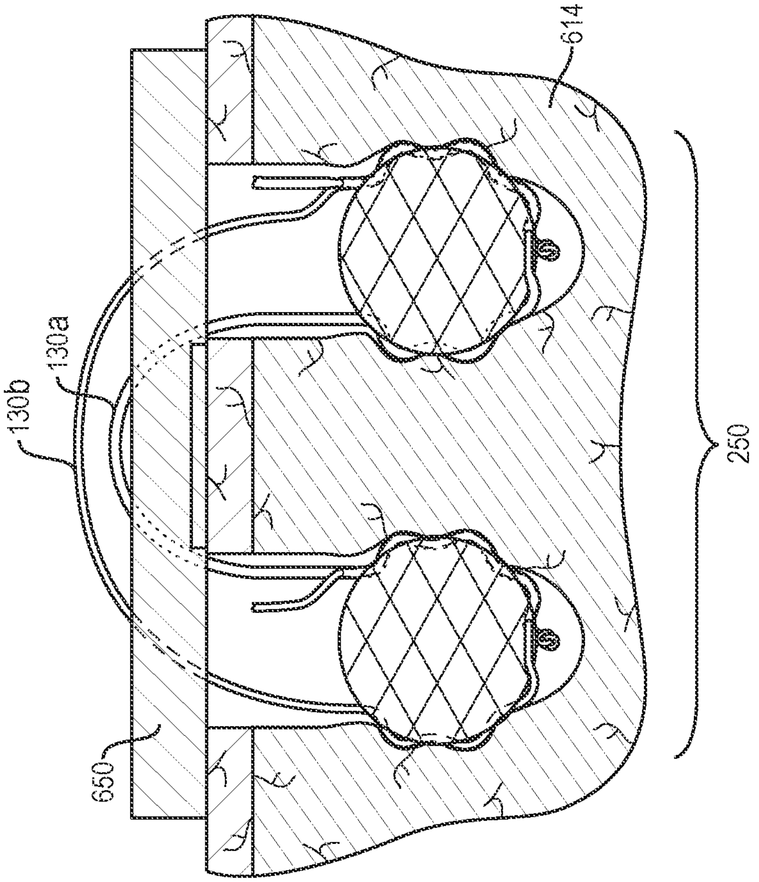
FIGS. 6A and 6B illustrate a method of attaching a sheet-like implant to a tendon of the shoulder with a soft anchor knotless suture staple construct; in accordance with this disclosure.
Figure 6A:
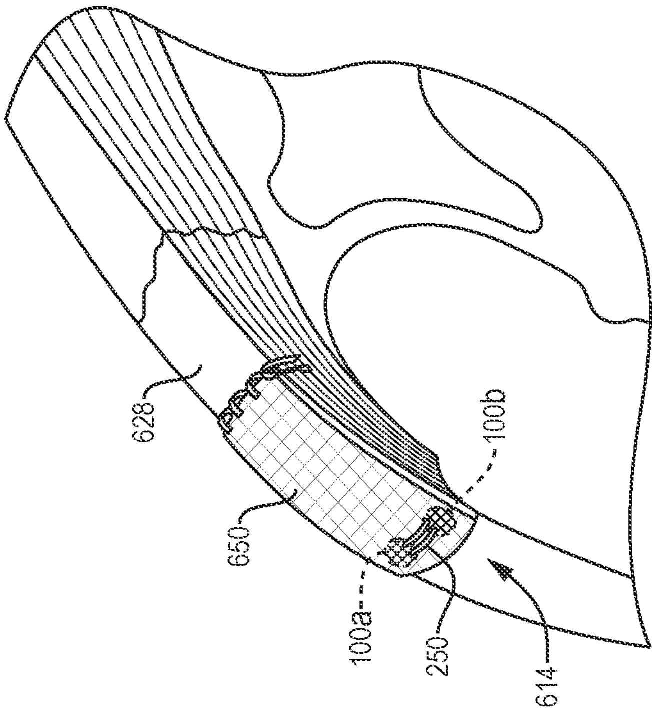

FIG. 6A is a stylized perspective view of a shoulder including a supraspinatus tendon 628 with a sheet-like implant 650 fixed thereto. Implant 650 may comprise, for example, various sheet-like structures without deviating from the spirit and scope of the present detailed description. In some useful embodiments, the sheet-like structure may comprise a plurality of fibers. The fibers may be interlinked with one another. When this is the case, the sheet-like structure may comprise a plurality of apertures comprising the interstitial spaces between fibers. Various processes may be used to interlink the fibers with one another. Examples of processes that may be suitable in some applications including weaving, knitting, and braiding. In some embodiment, the sheet-like structure may comprise a laminate including multiple layers of film with each layer of film defining a plurality of micro-machined or formed holes. The sheet-like structure of the tendon repair implant may also comprise a plurality of electro-spun nanofiber filaments forming a composite sheet. Additionally, the sheet-like structure may comprise a synthetic sponge material that defines a plurality of pores. The sheet-like structure may be a bio-inductive implant that may be places over a partial tear in the tendon.

Constructs 100, 145 and or 155 may be employed to fix implant 650 to distal tendon 628 for tendon repair. In the exemplary embodiment of FIG. 6A, a plurality of constructs 100*a*, 100*b* may be implanted into the humerus 614. Bone holes within the humerus 614 may first be prepared. A suture staple 250 may then be formed in accordance with the disclosure, the constructs 100*a*, 100*b* placed through the implant 650, as shown in FIG. 6B. Both constructs 100*a*, 100*b* may knotless lock with the opposite constructs repair suture. Constructs 100*a*, 100*b* may advantageously provide strong fixation of the implant 650 to the humerus 614 with a soft anchor construct, that requires minimal amount of bone removal.

Figure 7:
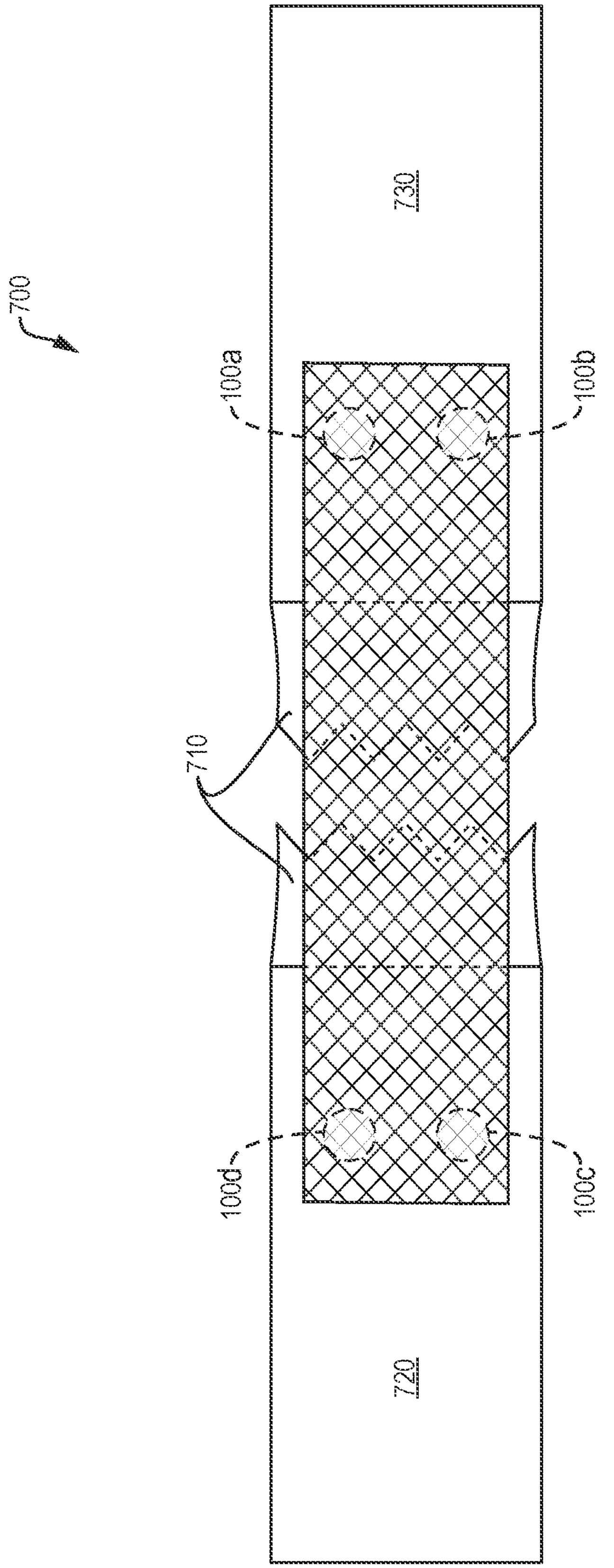
FIG. 7 illustrates a method of AC Joint repair with a knotless soft anchor linking construct, in accordance with this disclosure.

FIG. 7 illustrates a method of repair of an AC joint 700 and may include forming a knotless soft anchor chain construct, similar to that shown in FIG. 3. In one embodiment, an implant 750, which may be a sheet-like structure and may be a bio-inductive implant may be placed over a torn AC ligament 710. The implant 750 may be coupled to the acromion 720 and also the clavicle 730, via construct 100*a*, 100*b*, 100*c*, 100*d*. The knotless suture anchor constructs 100*a*, 100*b*, 100*c* and 100*d* may be implanted through the bio-inductive implant 750 that spans the acromion 720 and clavicle 730. In this embodiment, four knotless constructs 100*a*, 100*b*, 100*c* and 100*d* are used to secure the four corners of the bio-inductive implant 750. Other quantities in different arrangements as disclosed herein may also be employed. The knotless suture constructs 100*a*, 100*b*, 100*c* and 100*d* may be inserted through the bio-inductive implant 750 and then embedded within the underlying bone. The repair sutures (not shown) may form a daisy chain, as illustrated in FIG. 3, creating a rectangular arrangement of repair sutures holding tension on the bio-inductive implant 750 to the bone below. This may advantageously provide strong fixation with a soft anchor construct, that requires minimal amount of bone removal. This may advantageously provide strong fixation of the bio-inductive material 750 with an all-suture knotless anchor construct, that requires minimal amount of bone removal. Having the daisy chain arrangement may span repair sutures across the torn ligament 710 which may aid in further augmenting any repair of the ligament 710. In other example methods, the ligament 710 may only be partially torn. In other methods of AC joint repair, the repair may be absent an implant 750, and the repair sutures (130*a*, 130*b*, 130*c*, 130*d*) alone may form the repair. Each construct 100*a*, 100*b*, 100*c* and 100*d* may be implanted and deployed directly with the bones of the AC joint 700 and then may be coupled to each other in a chain (daisy or cross-over), the repair sutures fixing the two bones (720, 730) in the target location.

Figure 8:
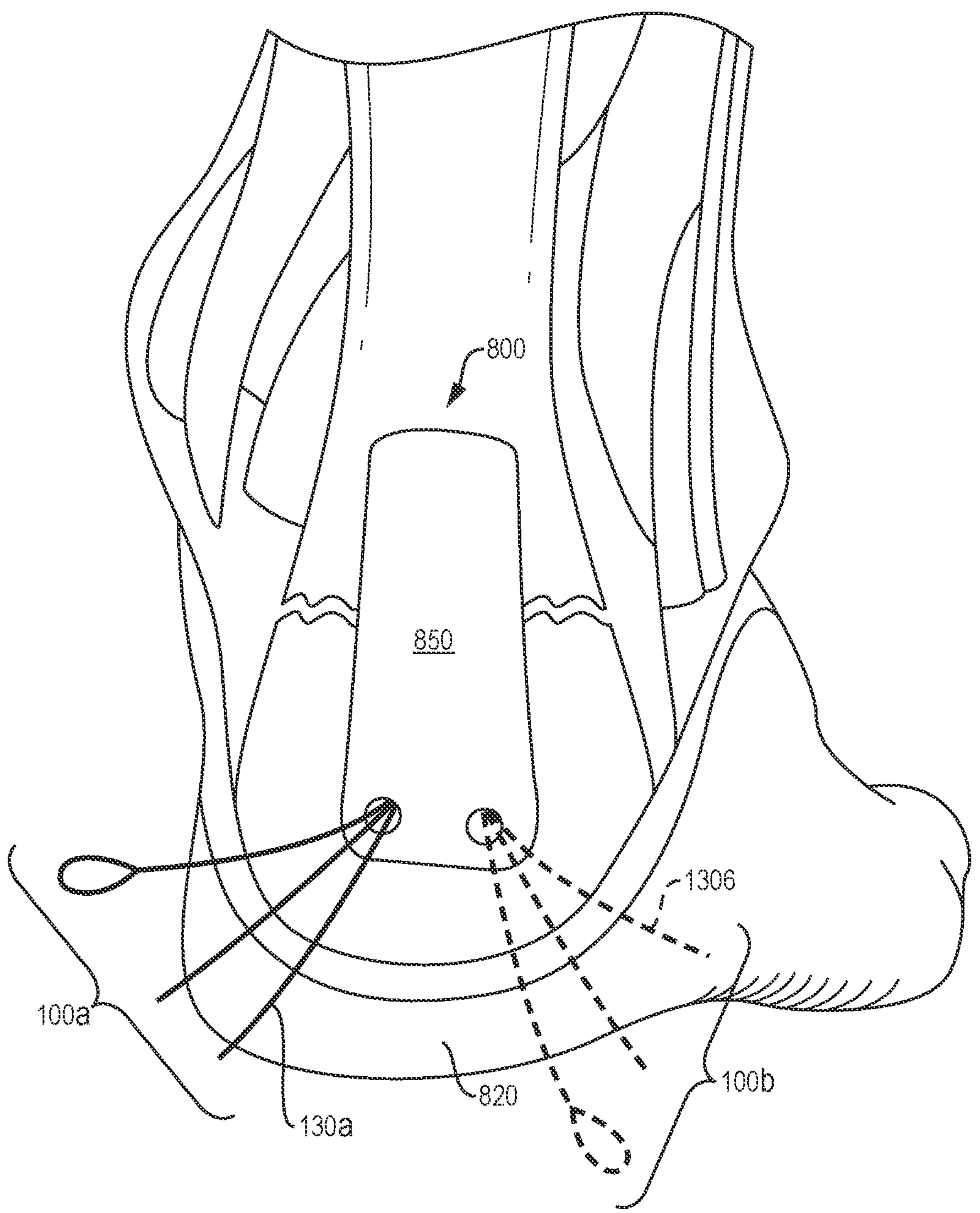
FIG. 8 illustrates a method of Achilles repair with a sheet like implant and a knotless soft anchor staple construct, in accordance with this disclosure.

FIG. 8 illustrates a method of repair of the Achilles 800, in a similar manner to repair shown in FIGS. 6A-6B and FIG. 7. The soft suture knotless constructs 100*a*, 100*b* may form a suture staple construct 250, as illustrated in FIG. 2D. Each knotless soft anchor construct 100*a*, 100*b* may be implanted through the bio-inductive implant 850 on the medial and side of the underlying calcaneus 820. Repair sutures 130*a*, 130*b* are tightened, creating a suture staple repair 250 holding the bio-inductive implant 850 to the bone below. This may advantageously provide strong fixation of the bio-inductive material 850 with an all-suture knotless anchor construct, that requires minimal amount of bone removal. A similar method may be used to repair the Gluteus Medius to the femur, wherein at least two constructs such as a combination of constructs (100, 145, 155) may be inserted through a sheet like implant similar to implant 850 to couple the implant 850 to the femur. The sheet-like implant may also be fixed to the Gluteus Medius to support repair thereof.

Figure 9:
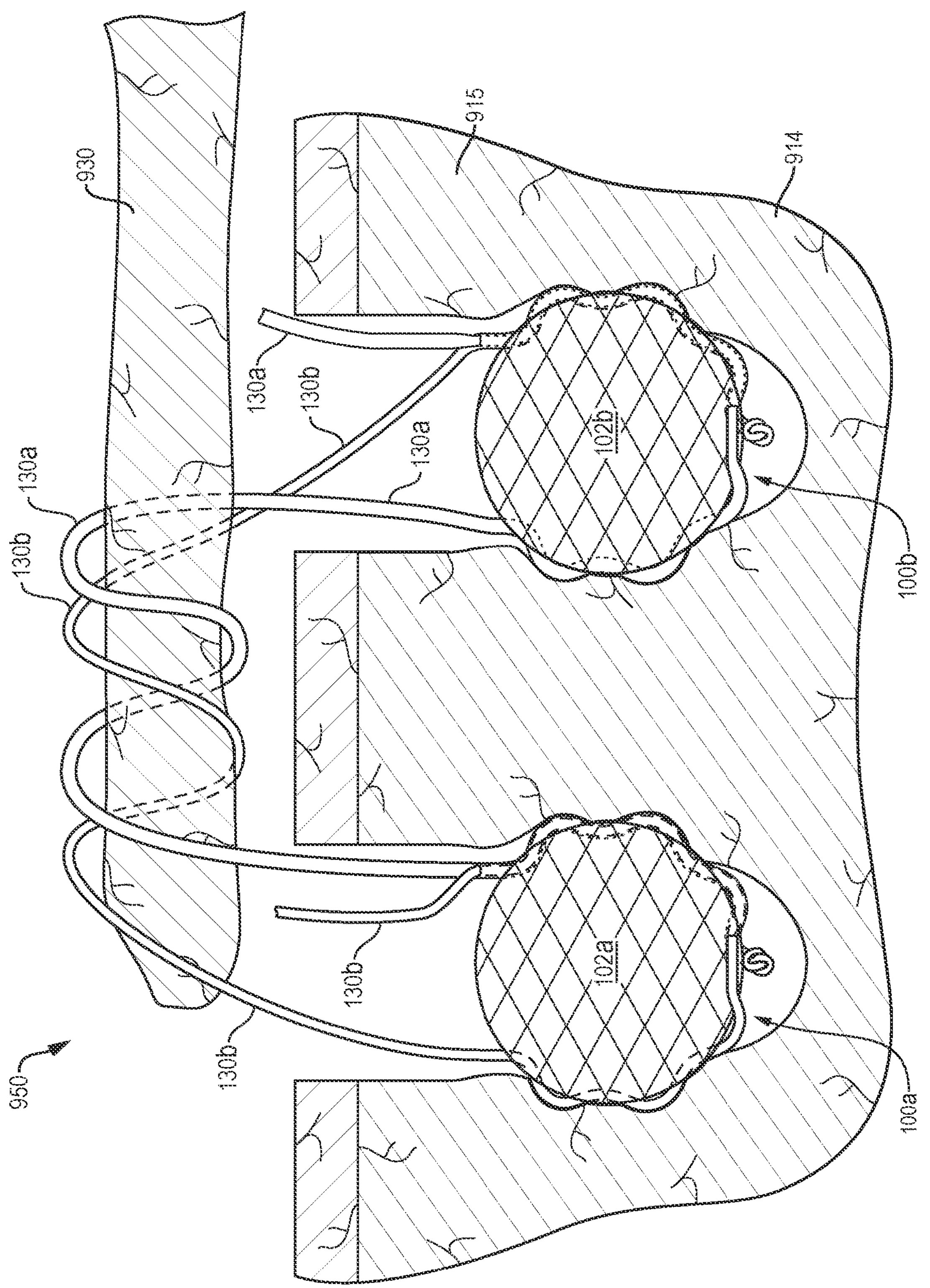
FIG. 9 illustrates a method of bicep tenodesis repair with the knotless soft anchor staple construct, in accordance with this disclosure.

FIG. 9 illustrates a method of knotlessly repairing a bicep tendon 930 to the humerus 914. A modified suture staple construct 950 is illustrated. The knotless anchor constructs 100*a*, 100*b* may both be implanted into the bicipital groove 915 of the humerus 914. The repair sutures 130*a*, 130*b* may then be passed some number of times through the bicep tissue 930 before being shuttled through the other anchor. In other example methods, the repair sutures 130*a*, 130*b* may be only positioned over the tendon 930, and may not extend through it, similar to the staple construct 250. The sutures are tightened, pulling the tendon 950 to the bone surface, forming a modified all-suture knotless staple 950, as illustrated in FIG. 9. This application would eliminate the need to tie knots, which may make this procedure easier. This may advantageously provide strong fixation with an all-suture anchor construct, that requires minimal amount of bone removal.

Figure 10A:
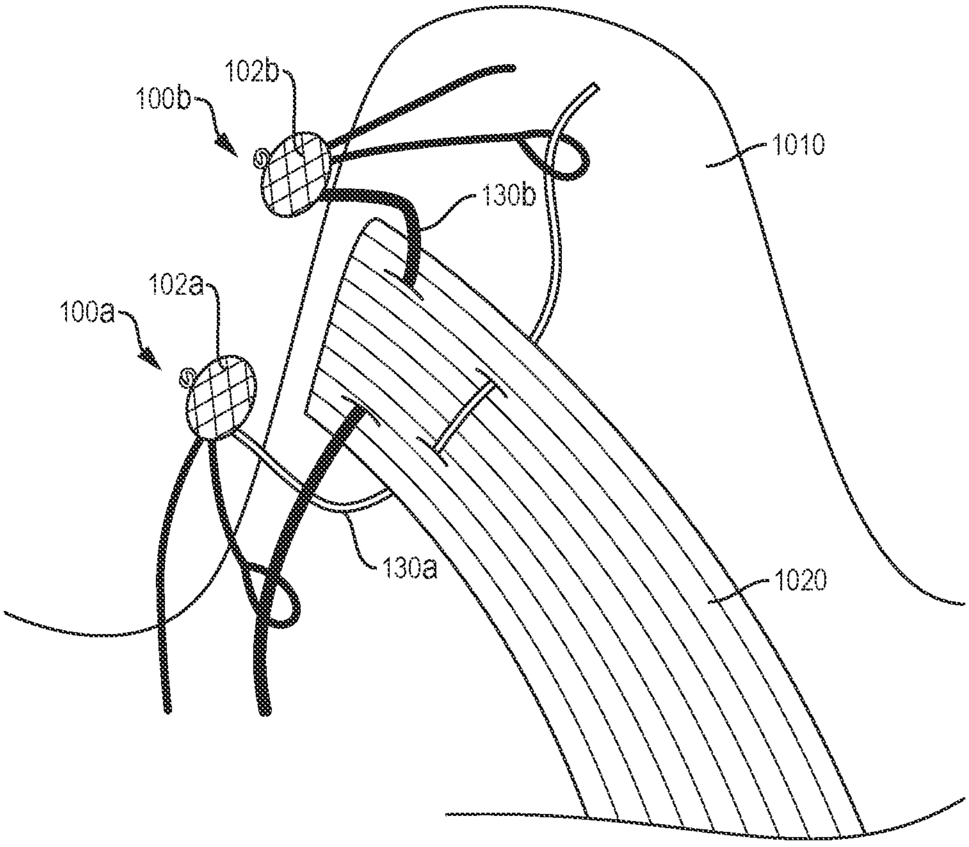
FIGS. 10A-10C illustrate a method of ACL repair with the knotless soft anchor staple construct, in accordance with this disclosure.
Figure 10B:
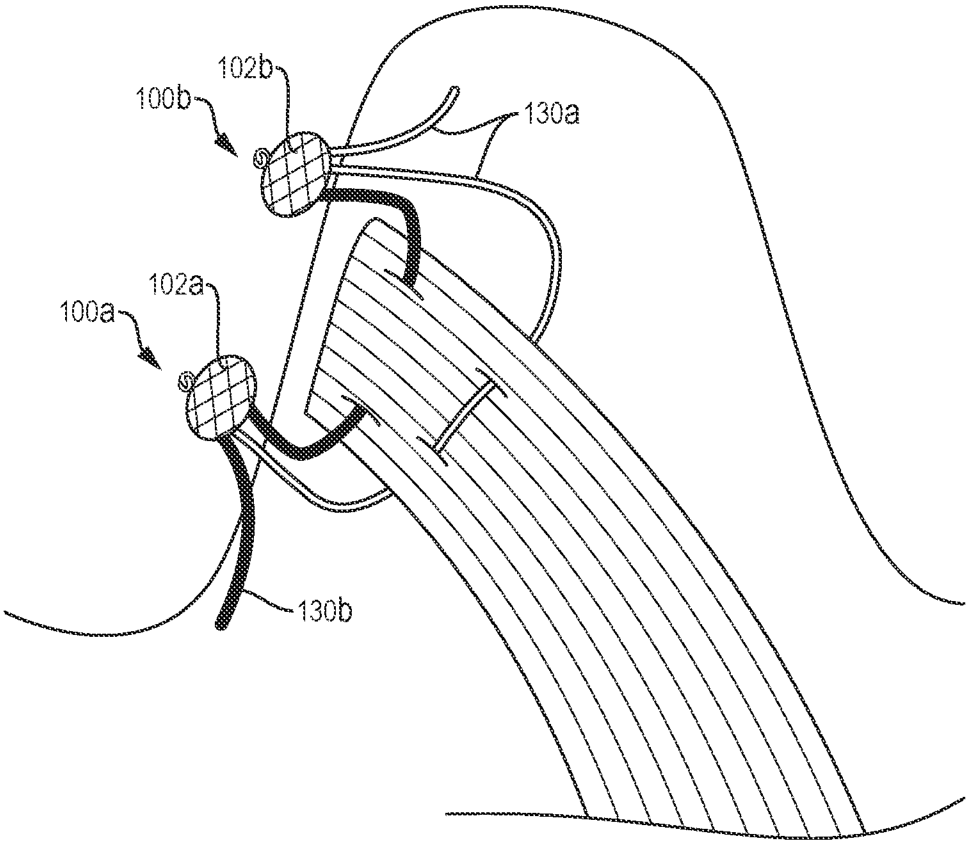
Figure 10C:
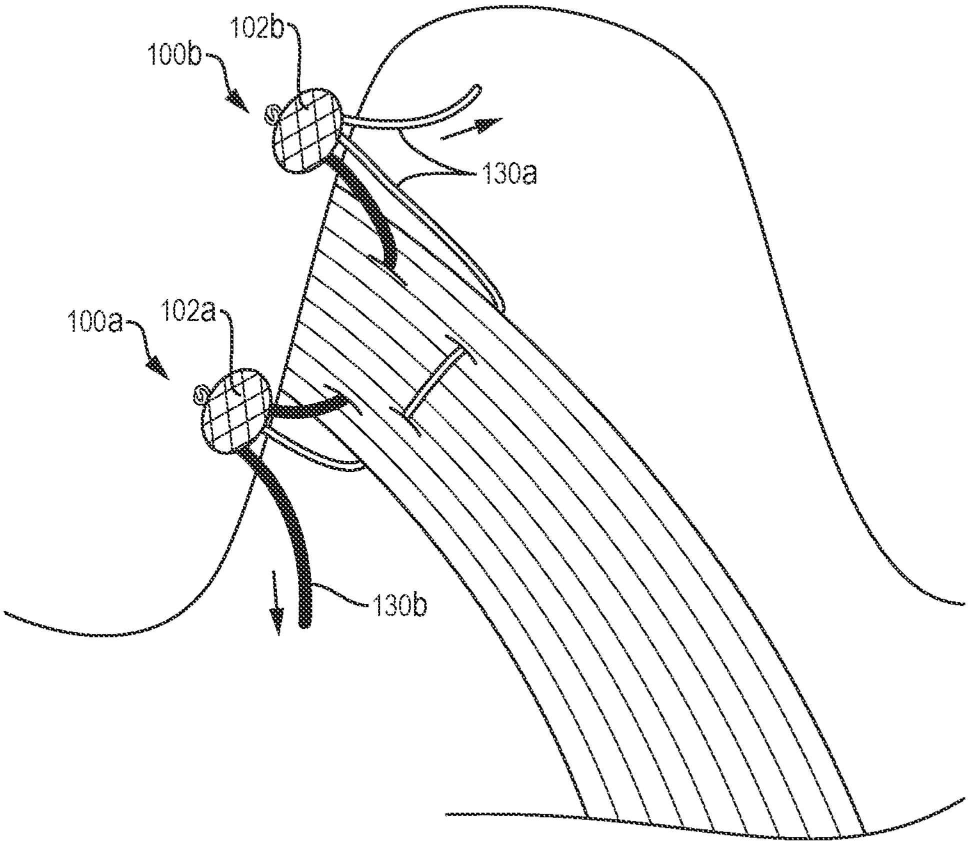

FIG. 10A-10C illustrate a method of ACL repair (Grade 1 or grade 2) with a plurality of soft anchor knotless constructs, that may be formed in a suture staple 250. Anchors 102*a* and 102*b* may be implanted into femur 1010 or, as illustrated may be placed on an external surface of femur 1010 and therefore act more like a cortical button style anchor. Anchors 102*a*, 102*b* may be placed adjacent an insertion location of the ACL 1020. Repair sutures 130*a*, 130*b* may be passed through ACL 1020 several times (similar to modified suture staple 950) and then passed through the opposite other construct 100*a*, 100*b*, to form a modified staple construct 250. Tension on repair suture 130*a*, 130*b* then fixedly coupled ACL 1010 to femur. Advantageously, the footprint for this ACL is small, therefore a smaller diameter implant is desirable. Additionally, the ability to utilize the anchors 102*a*, 102*b* as cortical bone anchor for fixation strength is a benefit, as there is a high load requirement on the repaired construct. This approach may be compatible with curved guides and drills, making access to the implant site easier than more rigid knotless suture anchors.

Figure 11:
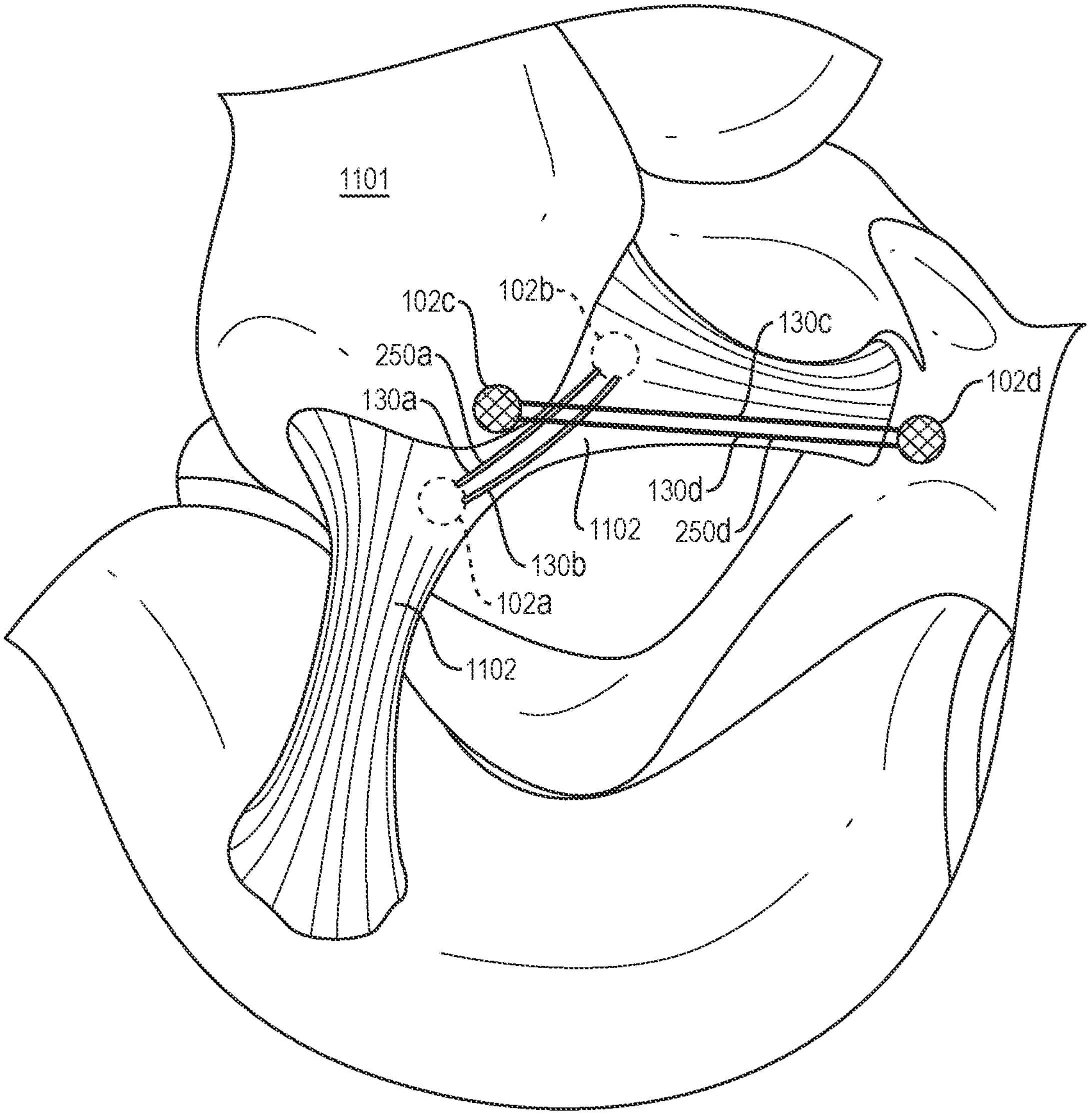
FIG. 11 illustrates a method of primary and secondary (augmentation) repair with the knotless soft anchor staple construct, in accordance with this disclosure.

FIG. 11 illustrates both a primary repair of a ligament with a first suture staple construct 250*a* and augmentation of the primary repair with a second suture staple construct 250*b*. Either primary repair or augmentation may be employed independently of other repair or augmentation constructs. First staple construct 250*a* includes placing anchors 102*a*, 102*b* in a distal end of fibula 1101 and laying ligament 1102 over the anchors 102*a*, 102*b*. Repair sutures 130*a*, 130*b* may be provided with needles attached to pierce ligament 1102. Repair sutures 130*a*, 130*b* preferably extend over and along an external surface of ligament 1102 to re-attach the ligament 1102 to the fibula 1101. Repair sutures 130*a*, 130*b* may stitch through ligament 1102 several times, similar to the modified suture staples (950) disclosed herein. Second staple construct 250*b* may be separate from first staple construct 250*a*. Second staple construct 250*b* is configured to augment the primary repair. Second staple construct 250*b* may be placed over first staple construct 250*a*. Second construct 250*b* may be tensioned to include some slack compared with first staple construct 250*a*, to provide a back-up upon excessive flexion of primary repair. In other embodiments at least one of the first or second repair construct may be a linking bridge similar to construct 450.

Advantageously the footprint for the attachment site for this primary repair is small, therefore a smaller diameter anchor 102 is desirable. Additionally, the ability to utilize the cortical bone for fixation strength is a benefit, as there is a high load requirement on the construct. Finally, this approach has lower risk to adjacent structures as the constructs are formed of all-suture.

Figure 12A:
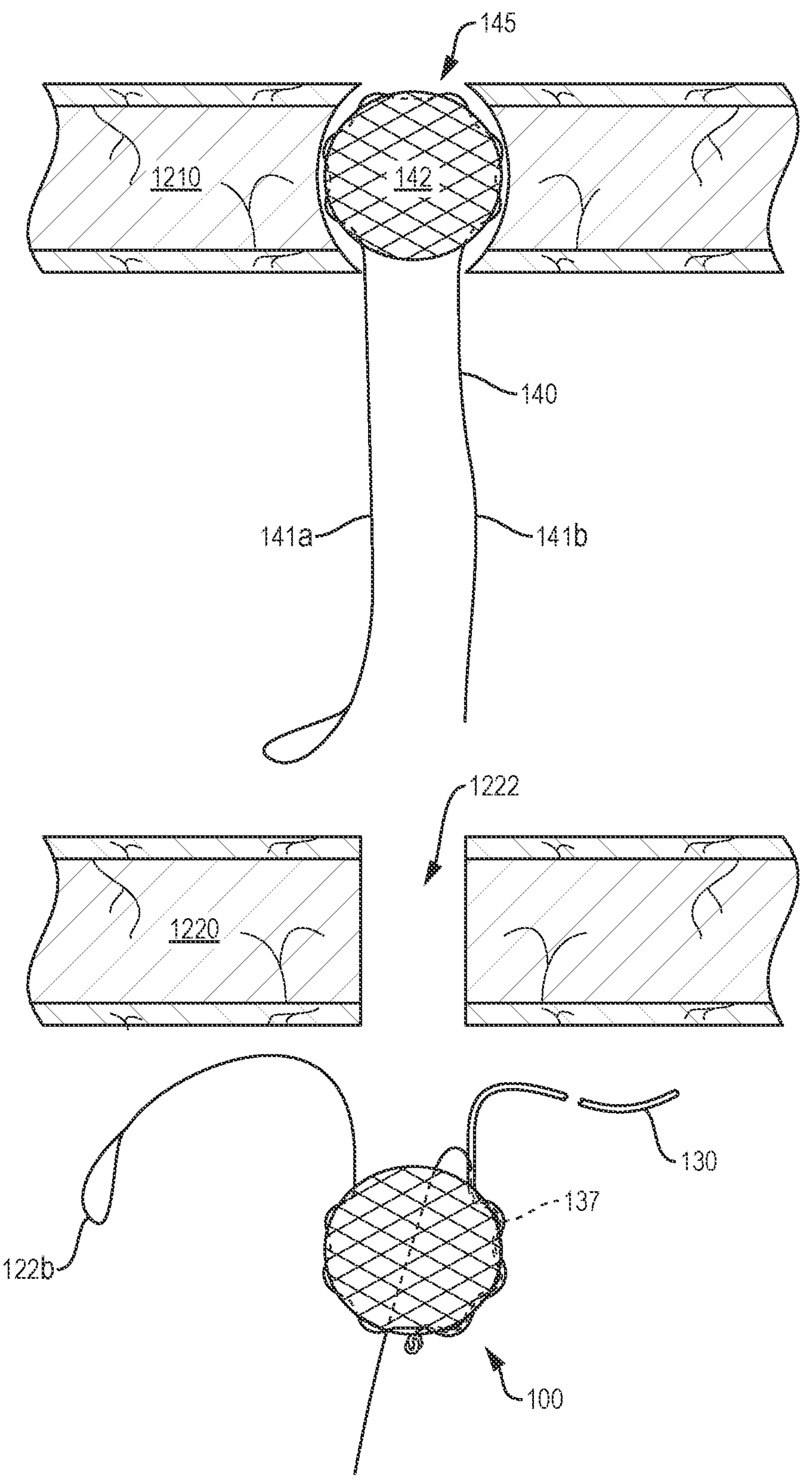
FIGS. 12A-12C illustrate another method of repair with a multiple soft anchor knotless construct, in accordance with the disclosure.
Figure 12B:
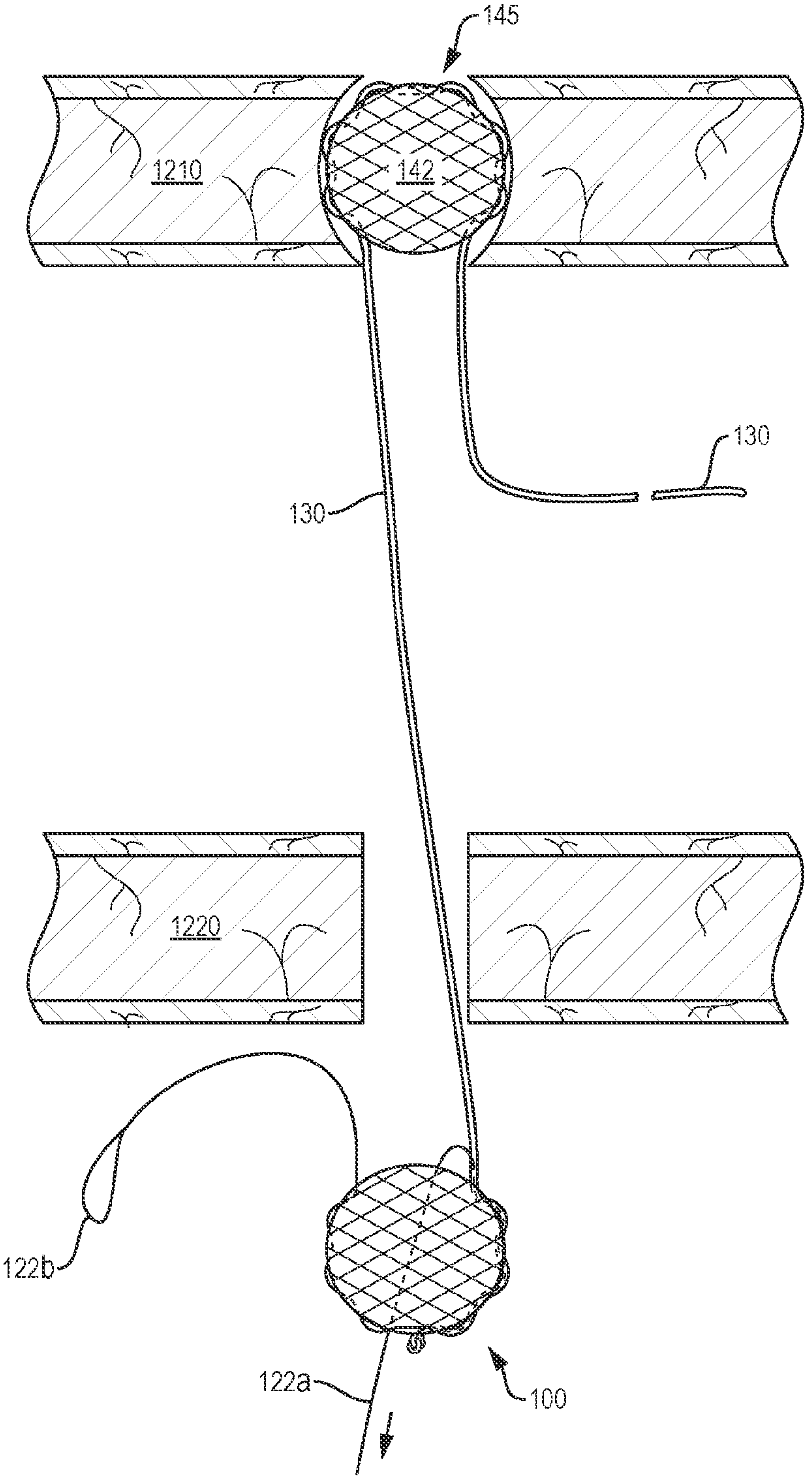
Figure 12C:
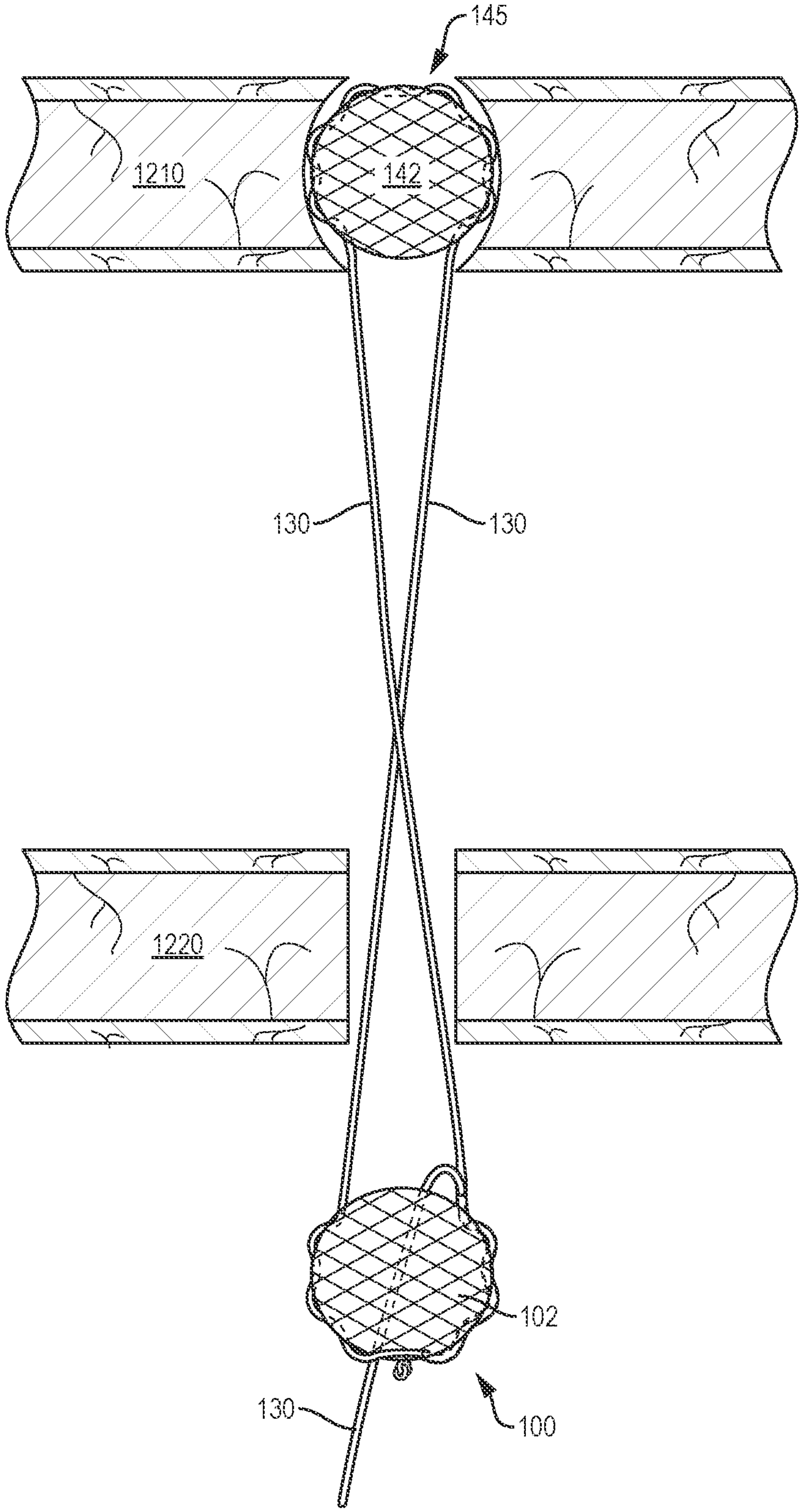

Turning now to FIGS. 12A-12C, repair may include repair of two bones (1210, 1220) that are elongate and extend parallel to each other. Bones such as the coracoid and clavicle in the AJ joint are approximately arranged this way. Bones such as the fibula and tibia may be arranged this way, adjacent the ankle syndesmosis. Repairing may include fixing a relative position of a first bone 1210 to a second bone 1220 with two anchors. A first anchor 142 may be placed first and may be pulley construct 145. First anchor 142 may be placed within a bone tunnel or on an external surface of the first bone 1210 (shown within the bone). First anchor 142 may be accessed by inserting it through a prepared tunnel 1222 of the second bone 1220 first. First anchor construct 145 may be placed on a furthest external surface, the surface facing away from the second bone 1220, as shown. Axially aligned tunnels may be prepared first through the two bones 1210, 1220. After the first anchor construct 145 is deployed, as shown in FIG. 12A, suture end 141*a* may couple to repair suture 130 of second anchor construct that may be similar to construct 100. Deploying the first anchor 142 to couple it to the first bone 1210 may include applying tension to the suture 140 in a direction towards the second bone 1220. Deploying the first anchor 142 to couple it to the first bone 1210 may include applying tension to the suture 140 with a first anchor construct insertion instrument inserted through the second bone 1220 (not shown). Suture 140 may then shuttle repair suture 130 through the first bone 1210 and through the first anchor 142. This removes the first anchor deploying suture 140 (FIG. 12B). The repair suture 130 may then be coupled to suture end 122*a* to shuttle the repair suture 103 back through construct 100. During this step, the repair suture 130 may be drawn from a first end (top end in figure) through and along a first side of the second anchor 102, then across to an opposing side of the anchor 102. It may concomitantly extend back to the first end, interweaving repeatedly through the opposing anchor side before extending through a lumen of second anchor 102 to extend from a second end (bottom end in the figure) of the anchor 1202, opposite the first end.

This configuration is shown in FIG. 12C. Further tensioning of the repair suture 130 after drawing it through the second anchor 102 may draw the first and second bones (1210, 1220) towards each other. Further tensioning of the repair suture 130 after drawing it through the second anchor 102 may draw the repair suture 130 through a repair suture splice length 137 disposed within the second anchor 102. Tensioning the repair suture 130 may therefore knotlessly lock the repair suture splice and therefore lock the repair construct. Tensioning the repair suture 130 may deploy the second anchor 102. In some embodiment, a separate suture (not shown) may operatively couple to the second anchor 102 to deploy it separately. Coupling the repair suture 130 to a transfer member 120 of the second anchor 102 may include coupling the repair suture 130 to a shuttling suture loop disposed at a first end of the second anchor 102 and wherein drawing the repair suture 130 through the second anchor 102 including drawing a second opposing end (122*a*) of the shuttling suture 122 away from an opposing end of the second anchor 102, away from the first and second bone (1210, 1220). Coupling the first anchor construct 145 may include anchoring the first anchor 142 within the first tunnel. Coupling the second anchor 102 may include anchoring the second anchor 102 within the second bone 1220. The splice length may interweave repeatedly through a single circumferential side of the second anchor 102.

One skilled in the art will realize the disclosure may be embodied in other specific forms without departing from the spirit or essential characteristics thereof. The foregoing examples are therefore to be considered in all respects illustrative rather than limiting of the disclosure described herein. Scope of the disclosure is thus indicated by the appended claims, rather than by the foregoing description, and all changes that come within the meaning and range of equivalency of the claims are therefore intended to be embraced therein.

What is claimed is:

1. A method of forming a knotless suture staple, comprising:

deploying a first soft anchor in a first bone portion, the first soft anchor being a tubular body defining a lumen and comprising a first repair suture extending therethrough, the first repair suture including a cannulation, and wherein the first soft anchor also includes a first deploying suture threaded through the first soft anchor and also through the cannulation defining a first knotless suture-locking-passage region, the first repair suture including the first knotless suture-locking-passage region interwoven repeatedly through and along a single side of the tubular body lumen and absent an opposing side of the tubular body lumen, wherein deploying includes applying tension to the first deploying suture;

deploying a second soft anchor in a second bone portion, spaced away from the first bone portion, the second soft anchor comprising a second repair suture extending therethrough, the second repair suture including a cannulation, and wherein the second soft anchor also includes a second deploying suture threaded through the second soft anchor and also through the cannulation of the second repair suture defining a second knotless suture-locking-passage region, the second knotless suture-locking-passage region interwoven repeatedly through and along the second soft anchor, wherein deploying includes applying tension to the second deploying suture;

with both soft anchors deployed, passing the first repair suture through the second soft anchor by:

coupling the first repair suture to the second deploying suture; and withdrawing the second deploying suture to remove the second deploying suture from the second soft anchor and replace it with the first repair suture, including drawing the first repair suture through the second knotless suture-locking-passage region to form a first leg of the knotless suture staple; and passing the second repair suture through the first soft anchor by:

coupling the second repair suture extending from the second soft anchor to the first deploying suture; and withdrawing the first deploying suture to remove it from the first soft anchor, and replace it with the second repair suture including drawing the second repair suture through the first knotless suture-locking-passage region to form a second leg of the knotless suture staple; and tensioning the first and second repair sutures to knotless lock the first and second legs of the knotless suture staple.

2. The method of claim 1 further comprising obtaining a bio-inductive sheet-like implant and wherein tensioning the first and second repair suture to knotless lock the knotless suture staple, staples the bio-inductive sheet-like implant to the first and second bone portions.

3. The method of claim 2 further comprising passing the first repair suture through the bio-inductive sheet-like implant and along an outer surface of the bio-inductive sheet-like implant, before coupling the first repair suture to the second deploying suture.

4. The method of claim 3 further comprising passing the second repair suture through the bio-inductive sheet-like implant and along an outer surface of the bio-inductive sheet-like implant, before coupling the second repair suture to the first deploying suture.

5. The method of claim 1 wherein the first and second bone are portions of a humerus bone, for repair of the supraspinatus tendon.

6. The method of claim 1 wherein the first and second bone portions are portions of a calcaneus for repair of an Achilles tendon.

7. The method of claim 1 wherein the first and second bone portions are portions of the femur adjacent a Gluteus Medius.

8. The method of claim 1 wherein the first bone portion is a distal end of a fibula and the second bone portion is a talus and wherein passing the first repair suture through the second soft anchor passes the first repair suture first along an exterior surface of the Anterior Talofibular Ligament over to the second soft anchor, and wherein tensioning the first and second repair suture to knotless lock the knotless suture staple, tensions the suture staple at a target tension that augments a primary repair of the Anterior Talofibular Ligament.

9. The method of claim 1 wherein the first repair suture includes a tape portion and wherein passing the first repair suture through the second soft anchor places the tape portion in engagement with a tissue to be repaired.

10. The method of claim 1 wherein the first and second soft anchor is also a tubular body, defining a lumen and where the second knotless suture-locking-passage region is interwoven through a single side of the second soft anchor lumen and absent an opposing side.

11. The method of claim 1 wherein the deploying the first soft anchor includes applying tension to both the first repair suture and first deploying suture, simultaneously.

12. A method of forming a knotless suture staple, comprising:

deploying a first soft anchor on an external surface of a first bone portion, the first soft anchor comprising a first repair suture extending therethrough, the first repair suture including a cannulation, and wherein the first soft anchor also includes a first deploying suture threaded through the first soft anchor and also through the cannulation defining a first knotless suture-locking-passage region, the first knotless suture-locking-passage region interwoven repeatedly through and along the first soft anchor, wherein deploying includes applying tension to the first deploying suture;

deploying a second soft anchor on a second bone portion, spaced away from the first bone portion, the second soft anchor comprising a second repair suture extending therethrough, the second repair suture including a cannulation, and wherein the second soft anchor also includes a second deploying suture threaded through the second soft anchor and also through the cannulation of the second repair suture defining a second knotless suture-locking-passage region, the second knotless suture-locking-passage region interwoven repeatedly through and along the second soft anchor, wherein deploying includes applying tension to the second deploying suture;

with both soft anchors deployed, passing the first repair suture through the second soft anchor by;

coupling the first repair suture to the second deploying suture; and withdrawing the second deploying suture to remove the second deploying suture from the second soft anchor, and replace it with the first repair suture, including drawing the first repair suture through the second knotless suture-locking-passage region to form a first leg of the knotless suture staple; and passing the second repair suture through the first soft anchor by:

coupling the second repair suture extending from the second soft anchor to the first deploying suture; and withdrawing the first deploying suture to remove it from the first soft anchor and replace it with the second repair suture including drawing the second repair suture through the first knotless suture-locking-passage region to form a second leg of the knotless suture staple; and tensioning the first and second repair sutures to knotless lock the first and second legs of the knotless suture staple.

13. The method of claim 12 wherein the first and second bone are portions are located opposing sides of an ACL insertion location.

14. The method of claim 13 further comprising coupling the first and second repair sutures to an ACL.

15. A method of forming a knotless suture staple, comprising:

deploying a first soft anchor in a first bone portion, the first soft anchor comprising a first repair suture fixedly coupled to the first soft anchor and extending through the first soft anchor with a first repair suture end extending from a proximal end of the first soft anchor, the first repair suture including a cannulation, and wherein the first soft anchor also includes a first deploying suture threaded through the first soft anchor and also through the cannulation defining a first knotless suture-locking-passage region, the first knotless suture-locking-passage region interwoven repeatedly through and along the first soft anchor, wherein deploying includes applying tension to the first deploying suture;

deploying a second soft anchor in a second bone portion, spaced away from the first bone portion, the second soft anchor comprising a second repair suture fixedly coupled to the second soft anchor and extending through the second soft anchor, with a proximal end extending from a proximal end of the second soft anchor, the second repair suture including a cannulation, and wherein the second soft anchor also includes a second deploying suture threaded through the second soft anchor and also through the cannulation of the second repair suture defining a second knotless suture-locking-passage region, the second knotless suture-locking-passage region interwoven repeatedly through and along the second soft anchor, wherein deploying includes applying tension to the second deploying suture;

with both soft anchors deployed, passing the first repair suture end through the second soft anchor by:

coupling the first repair suture end to the second deploying suture; and withdrawing the second deploying suture to remove the second deploying suture from the second soft anchor and replace it with the first repair suture end, including drawing the first repair suture end through the second knotless suture-locking-passage region to form a first leg of the knotless suture staple; and passing the second repair suture end through the first soft anchor, by;

coupling the second repair suture end extending from the second soft anchor to the first deploying suture; and withdrawing the first deploying suture to remove it from the first soft anchor and replace it with the second repair suture end including drawing the second repair suture end through the first knotless suture-locking-passage region to form a second leg of the knotless suture staple; and tensioning the first and second repair suture ends to knotless lock the first and second legs of the knotless suture staple.

16. The method of claim 15 further comprising obtaining a bio-inductive sheet-like implant and wherein tensioning the first and second repair suture ends to knotless lock the knotless suture staple, staples the bio-inductive sheet-like implant to the first and second bone portions.

17. The method of claim 15 wherein the first repair suture end includes a tape portion and wherein passing the first repair suture end through the second soft anchor places the tape portion in engagement with a tissue to be repaired.

18. The method of claim 15 wherein the deploying the first soft anchor includes applying tension to both the first repair suture end and first deploying suture, simultaneously.

* * * * *